(12) United States Patent
Raber

(10) Patent No.: US 8,475,171 B2
(45) Date of Patent: Jul. 2, 2013

(54) OBJECT RECOGNITION TESTING TOOLS AND TECHNIQUES FOR MEASURING COGNITIVE ABILITY AND COGNITIVE IMPAIRMENT

(75) Inventor: Jacob Raber, Portland, OR (US)

(73) Assignee: Oregon Health & Science University, Portland, OR (US)

( * ) Notice: Subject to any disclaimer, the term of this patent is extended or adjusted under 35 U.S.C. 154(b) by 0 days.

(21) Appl. No.: 13/434,297

(22) Filed: Mar. 29, 2012

(65) Prior Publication Data
US 2012/0190968 A1 Jul. 26, 2012

Related U.S. Application Data

(62) Division of application No. 11/888,091, filed on Jul. 30, 2007, now abandoned.

(60) Provisional application No. 60/928,577, filed on May 9, 2007.

(51) Int. Cl.
G09B 19/00 (2006.01)

(52) U.S. Cl.
USPC ............................ 434/236; 434/323; 434/350

(58) Field of Classification Search
USPC ........................... 434/236, 350, 323; 600/300
See application file for complete search history.

(56) References Cited

U.S. PATENT DOCUMENTS

| 5,911,581 | A * | 6/1999 | Reynolds et al. ............. 434/236 |
| 6,186,145 | B1 | 2/2001 | Brown |
| 6,306,086 | B1 | 10/2001 | Buschke |
| 6,364,845 | B1 | 4/2002 | Duffy et al. |
| 6,425,764 | B1 | 7/2002 | Lamson |
| 6,503,085 | B1 | 1/2003 | Elkind |
| 6,565,359 | B2 | 5/2003 | Calhoun et al. |
| 6,632,174 | B1 | 10/2003 | Breznitz |
| 6,663,392 | B2 * | 12/2003 | Leyva et al. .................. 434/236 |
| 6,688,746 | B2 | 2/2004 | Malov |
| 7,122,004 | B1 | 10/2006 | Cassily |
| 7,207,804 | B2 * | 4/2007 | Hersh ........................... 434/236 |
| 7,333,963 | B2 | 2/2008 | Widrow et al. |
| 7,645,140 | B2 | 1/2010 | Duffy et al. |
| 2002/0103428 | A1 | 8/2002 | deCharms |
| 2002/0103429 | A1 | 8/2002 | deCharms |
| 2002/0116352 | A1 | 8/2002 | Kilgard et al. |
| 2002/0120208 | A1 | 8/2002 | Kim et al. |
| 2002/0128540 | A1 | 9/2002 | Kim et al. |
| 2004/0092809 | A1 | 5/2004 | deCharms |
| 2004/0208923 | A1 | 10/2004 | Davis et al. |
| 2005/0019734 | A1 | 1/2005 | Peled |
| 2005/0033154 | A1 | 2/2005 | deCharms |

(Continued)

OTHER PUBLICATIONS

2nd Annual HIP Day, fellows and Faculty Clinical and Translational Research Symposium, Schedule, 1 page, (May 11, 2007).

(Continued)

*Primary Examiner* — Kang Hu
(74) *Attorney, Agent, or Firm* — Klarquist Sparkman, LLP

(57) ABSTRACT

Techniques and tools for measuring cognitive ability and/or detecting cognitive impairment or decline. For example, techniques and tools are described that can be used to diagnose or test susceptibility to cognitive impairments in children or in elderly people (such as cognitive impairments associated with Alzheimer's Disease). Techniques and tools are described that can be used to evaluate treatment effects and/or measure cognitive decline over time.

16 Claims, 14 Drawing Sheets

U.S. PATENT DOCUMENTS

| | | | |
|---|---|---|---|
| 2005/0096396 A1 | 5/2005 | Davis et al. |
| 2005/0175972 A1 | 8/2005 | Goldman et al. |
| 2005/0197560 A1 | 9/2005 | Rao et al. |
| 2005/0216243 A1 | 9/2005 | Graham et al. |
| 2005/0228785 A1 | 10/2005 | Wolcott et al. |
| 2005/0283053 A1 | 12/2005 | deCharms |
| 2006/0074340 A1 | 4/2006 | Murata |
| 2006/0161218 A1 | 7/2006 | Danilov |
| 2006/0241718 A1 | 10/2006 | Tyler et al. |
| 2006/0293617 A1 | 12/2006 | Einav et al. |
| 2007/0027406 A1 | 2/2007 | LaPlaca et al. |
| 2007/0088404 A1 | 4/2007 | Wyler et al. |
| 2007/0166675 A1 | 7/2007 | Atkins et al. |
| 2009/0118588 A1 | 5/2009 | Robinson et al. |

OTHER PUBLICATIONS

Acevedo et al., "Sex- and Histamine-Dependent Long-Term Cognitive Effects of Methamphetamine Exposure," Neuropsychopharmacology, pp. 665-672, (2007).
Astur et al, "A characterization of performance by men and women in a virtual Morris water task: A large and reliable sex difference," Elsevier Behavioural Brain Research, pp. 185-190, (1998).
Astur et al., "Sex differences and correlations in a virtual Morris water task, a virtual radial aim maze, and mental rotation," Elsevier Behavioural Brain Research, 13 pages, (2003).
Benice et al., "Sex-Differnences in Age-Related Cognitive Decline in C57BL/6J Mice Associated with Increased Brain Microtubule-Associated Protein 2 and Synaptophysin Immunoreactivity," Neuroscience, pp. 413-423, (Aug. 29, 2005).
Berteau-Pavy et al., "Effects of Sex and Apoe ∈4 on Object Recognition and Spatial Navigation in the Elderly," Neuroscience (Available online May 23, 2007).
Bookheimer et al., "Patterns of Brain Activation in People at Risk for Alzheimer's Disease," The New England Journal of Medicine, vol. 343, 7 pages, (Aug. 17, 2000).
Burgess et al., "A Temporoparietal and Prefrontal Network for Retrieving the Spatial Context of Lifelike Events," NeuroImage 14, pp. 439-453, (2001).
Corder et al., "Apolipoprotein E Genotype Determines Survival in the Oldest Old (85 Years or Older) Who Have Good Cognition," American Medical Association, vol. 53(5), pp. 418-422, (May 1996).
Darby, "Reaction Times," http://www.delphiforfun.org/Programs/Reaction_times.htm (©2000-2007).
Farrer et al., "Effects of age, sex, and ethnicity on the association between apolipoprotein E genotype and Alzheimer disease. A meta-analysis. APOE and Alzheimer Disease Meta Analysis Consortium," Am. Med. Assoc. vol. 278, pp. 1349-1356 (1997).
Frucht, "Israeli researcher at forefront of virtual reality technology," Israel21c A focus Beyond, http://www.israel21c.org/bin/en.jsp?enScript=PrintVersion.jsp&enDispWho=Articles1946, 3 pages, (Mar. 20, 2005).
Grön et al., "Brain activation during human navigation: gender-different neural networks as substrate of performance," Nature Neuroscience, vol. 3, No. 4, 5 pages, (Apr. 2000).
Kurlowicz et al., "The Mini Mental State Examination (MMSE)," Try This: Best Practices in Nursing Care to Older Adults, Hartford Institute for Geriatric Nursing, No. 3 (Jan. 1999).
Levy et al, "Men and Women Differ in Object Memory but Not Performance of a Virtual Radial Maze," Behavioral Neuroscience, vol. 119, No. 4, pp. 853-862, (2005).
Mahley, "Apolipoprotein E: cholesterol transport protein with expanding role in cell biology," Science, vol. 240, pp. 622-630, (1988).
Moffat et al., "Age differences in spatial memory in a virtual environment navigation task," Elsevier Neurobiology of Aging, pp. 787-796, (2001).
Moffat et al., "Effects of Age on Virtual Environment Place Navigation and Allocentric Cognitive Mapping," Behavioral Neuroscience, vol. 116, No. 5, pp. 851-859, (2002).
Moffat et al., "Longitudinal Assessment of Serum Free Testosterone Concentration Predicts Memory Performance and Cognitive Status in Elderly Men," The Journal of Clinical Endocrinology & Metabolism, 7 pages, (2002).
"Motion Blindness,' Not Just Poor Memory, Causes Alzheimer's Patients to Lose Their Way," University of Rochester News, 3 pages, (Mar. 22, 1999).
Pfankucha et al., "Role of circulating androgen levels in effects of apoE4 on cognitive function," Elsevier Brain Research, 9 pages (Jun. 10, 2005).
Raber et al., "Androgens Protect against Apolipoprotein E4-Induced Cognitive Deficits," The Journal of Neuroscience, 6 pages (Jun. 15, 2002).
Raber et al., "Apolipoprotein E and cognitive performance," Nature, vol. 404, pp. 352-354, (Mar. 23, 2000).
Raber et al., "Isoform-specific effects of human apolipoprotein E on brain function revealed in ApoE knockout mice: Increased susceptibility of females," Proc. Natl. Acad. Sci. USA, vol. 95, pp. 10914-10919, (Sep. 1998).
Raber, "Androgens, ApoE, and Alzheimer's Disease," SAGE KE, pp. 1-11, (Mar. 17 2004).
Rizk-Jackson et al, "Effects of sex on object recognition and spatial navigation in humans," pp. 181-190, (2006).
Rizzo et al., "Simulated Car Crashes at Intersections in Drivers With Alzheimer Disease," Alzheimer Disease and Associated Disorders, vol. 15, No. 1, pp. 10-20, (2000).
Robertson et al., "apoE isoforms and measures of anxiety in probable AD patients and Apoe-/- mice," Elsevier Neurobiology of Aging, pp. 637-643, (2004).
Steffin, "Virtual Reality: Overview of its Application to Neurology," http://www.emedicine.com/neuron/topic463.htm, 7 pages, (Oct. 11, 2006).
Takacs, "Cognitive, Mental and Physical Rehabilitation Using a Configurable Virtual Reality System," The International Journal of Virtual Reality, 11 pages, (2006).
Turic et al., "No association between apolipoprotein E polymorphisms and general cognitive ability in children," Neuroscience Letters, vol. 299, pp. 97-100, (2001).
Virtual Iraq—VR Based Therapy for Post-Traumatic Stress Disorder, Virtually Better, http://www.defense-update.com/products/v/CR-PTSD.htm, 2 pages, (Dec. 1, 2005).

\* cited by examiner

Figure 5
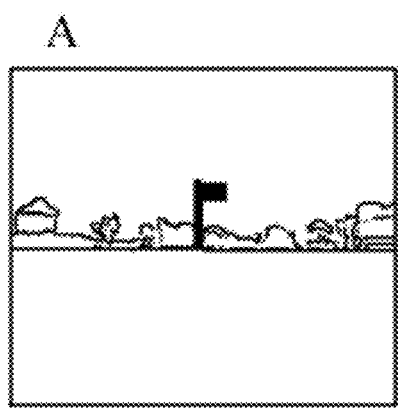
A
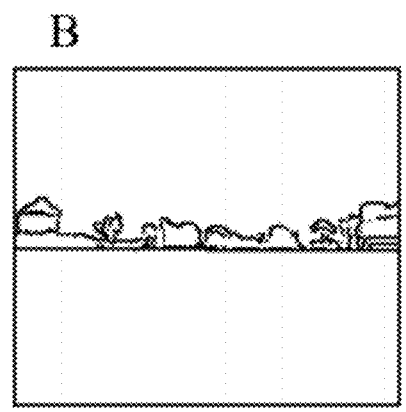
B
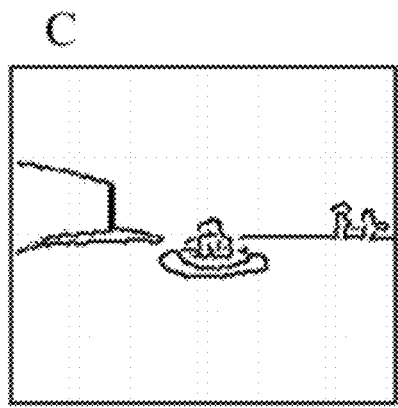
C
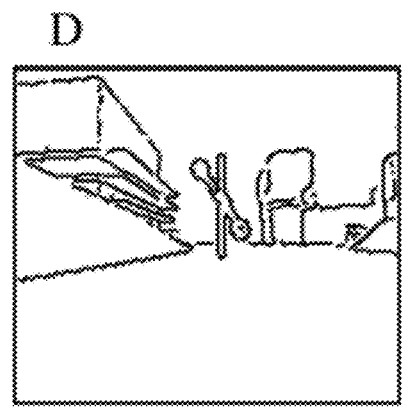
D
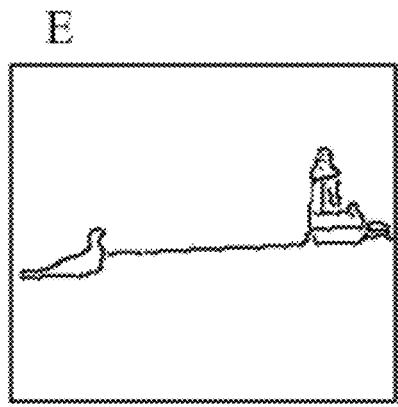
E
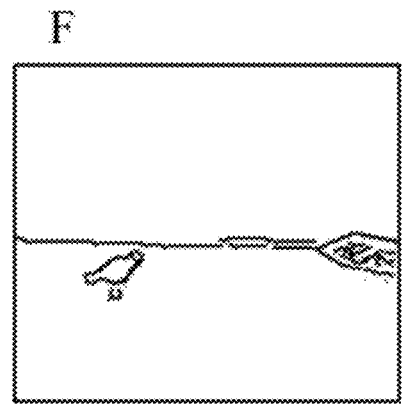
F

OBJECT RECOGNITION TESTING TOOLS AND TECHNIQUES FOR MEASURING COGNITIVE ABILITY AND COGNITIVE IMPAIRMENT

RELATED APPLICATION INFORMATION

This application is a divisional of U.S. patent application Ser. No. 11/888,091, filed Jul. 30, 2007, now abandoned which claims the benefit of U.S. Provisional Patent Application No. 60/928,577, entitled "Computer Software-Oriented Tools and Techniques for Measuring Cognitive Ability and Cognitive Impairment," filed May 9, 2007, the disclosures from both applications are incorporated by reference.

GOVERNMENT SUPPORT

The inventions described in this patent application were made in part by government support under NIH Grant # P30 AG08017. The United States Government may have rights in these inventions.

FIELD

The present disclosure relates to tools and techniques for measuring cognitive ability and/or impairment.

BACKGROUND

Many environmental and intrinsic factors influence cognitive function. Intrinsic factors that can influence cognitive function include sex, age and genetic makeup.
Sex Differences in Cognitive Function Effects of sex on cognitive function have been shown in humans and animal models using established tests. Sex differences have been demonstrated in both episodic memory tasks (favoring women) and spatial visualization tasks (favoring men). Interestingly, in some studies alcohol consumption abolished sex differences in spatial visualization, but not episodic memory performance. In addition, stress has been shown to differentially affect fear conditioning in men and women.

Consistent with the human studies, effects of sex on cognitive function have also been reported in animal models using established tests. In general, studies of spatial learning and memory in rodents have shown that males learn more quickly than females and exhibit superior performance in a variety of mazes. Some studies, however, have not shown such differences between the sexes. Sex differences in classical fear conditioning and shuttlebox avoidance conditioning in rats have also been reported. In addition, in some studies neonatal isolation facilitated appetitive response learning in adult female, but not male, rats.

Cognitive tests administered to humans and animals frequently involve large differences. Therefore, it often remains difficult to directly compare results on these tests across species. For example, while spatial learning and memory can be easily assessed in humans and animal models, to compare assessments of spatial learning and memory in humans and mice, navigation to a target can be important. In some tests of spatial memory, when all the information is within one field of view, the participant has an aerial perspective and a body-centered (egocentric) frame of reference (e.g. table-top tests of spatial memory). Such tests are routinely used to assess visuospatial memory, but are very different from tests of spatial memory typically used for rodents. Testing visuospatial memory in rodents typically involves a viewer perspective of a world-centered (allocentric) frame of reference with information found throughout a complex environment in which the participant has to navigate. Making direct inferences about performance on navigation tests from performance on table-top tests can be problematic.

Virtual reality ("VR"), which has been used to assess, expose, and desensitize (in phobias) event and place-related memories, to assess and teach driving and flying skills, and to distract in pain management, can also be used to assess spatial learning and memory in humans using a navigational task. Navigation in a virtual environment has been shown to be sensitive to effects of sex of participants in some, but not all, studies. In one study, a virtual environment consisting of a series of interconnected hallways, some leading to dead ends and others leading to a designated goal location, was used to study age and sex differences in spatial navigation. In this study, there was no significant effect of sex on time to complete the maze or total distance traveled, but there was an effect of sex on total number of deviations from the correct route into a dead-end corridor, and there was an effect of sex on how often participants traveled on a portion of the correct route through which they had already traveled. However, as there was no cued version of this test, it is difficult to distinguish task learning performance from spatial learning and memory performance. In another study from the same authors, a virtual water maze environment was used to study the effects of age and sex on spatial learning and memory in humans. (The water maze paradigm is commonly used to assess spatial learning and memory in rodents.) An effect of age, but not of sex, was detected on performance. In this study, a trial with a visible target was given following the trials with a hidden target.
Apolipoprotein E (APOE) Genotype and Age Differences in Cognitive Function The three major human isoforms of apolipoprotein E (APOE), which are encoded by distinct APOE alleles ($\epsilon2$, $\epsilon3$, and $\epsilon4$), are involved in the metabolism and redistribution of lipoproteins and cholesterol. Compared with $\epsilon2$ and $\epsilon3$, $\epsilon4$ is associated with increased risk of cognitive impairments and of developing Alzheimer's disease (AD). Women are at higher risk to develop AD than men, particularly women carrying $\epsilon4$. In contrast to the risk to develop AD, the effects of $\epsilon4$ on cognitive function in the non-demented elderly old-old (>75 years of age) are less clear. While some studies have shown poor cognitive performance in non-demented elderly $\epsilon4$ carriers compared with non-demented elderly non-$\epsilon4$ carriers and a small effect was observed in a meta-analysis, other studies did not.

In the elderly, high cortisol and low testosterone levels might contribute to reduced cognitive function. In older men and women, higher cortisol levels have been associated with poorer cognitive performance in some studies. However, in another study cortisol levels only inversely correlated with paragraph recall in older participants with mild cognitive impairment (MCI) but not in elderly control participants. APOE genotype might also influence cortisol levels. In AD patients, higher cerebrospinal cortisol levels in $\epsilon4$ than non-$\epsilon4$ carriers have been reported, although comparable cerebrospinal cortisol in non-$\epsilon4$ and $\epsilon4$ carriers have also been reported. In elderly men, low testosterone levels might also contribute to reduced cognitive function. In older men, testosterone levels have been positively correlated with cognitive function, and cognitive function could be improved by testosterone treatments. Similarly, testosterone, but not estrogen, levels in serum have correlated positively with cognitive performance in older women, and androgen therapy has been shown to improve cognition in surgically menopausal women. The relationship between testosterone levels and cognitive function might be ε4-dependent. In men, low testosterone levels and ε4 have been shown to interact in increasing the risk of developing AD. In addition, an interaction between ε4 and cognitive performance in healthy older men has been reported; while in non-ε4 carriers higher testosterone levels were associated with better general cognition, in ε4 carriers higher testosterone levels were associated with lower cognitive performance.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

In summary, the Detailed Description is directed to various techniques and tools for measuring cognitive ability and/or detecting cognitive impairment or decline. For example, techniques and tools are described that can be used to diagnose or test susceptibility to cognitive impairments in children or in elderly people (such as cognitive impairments associated with Alzheimer's Disease). Techniques and tools are described that can be used to evaluate treatment effects and/or measure cognitive decline over time.

The foregoing and other objects, features, and advantages of the invention will become more apparent from the following detailed description, which proceeds with reference to the accompanying figures.

BRIEF DESCRIPTION OF THE DRAWINGS

FIG. 5 is a diagram showing screen shots of a virtual reality, spatial navigation software tool according to one or more described embodiments.

DETAILED DESCRIPTION

Figure 1:
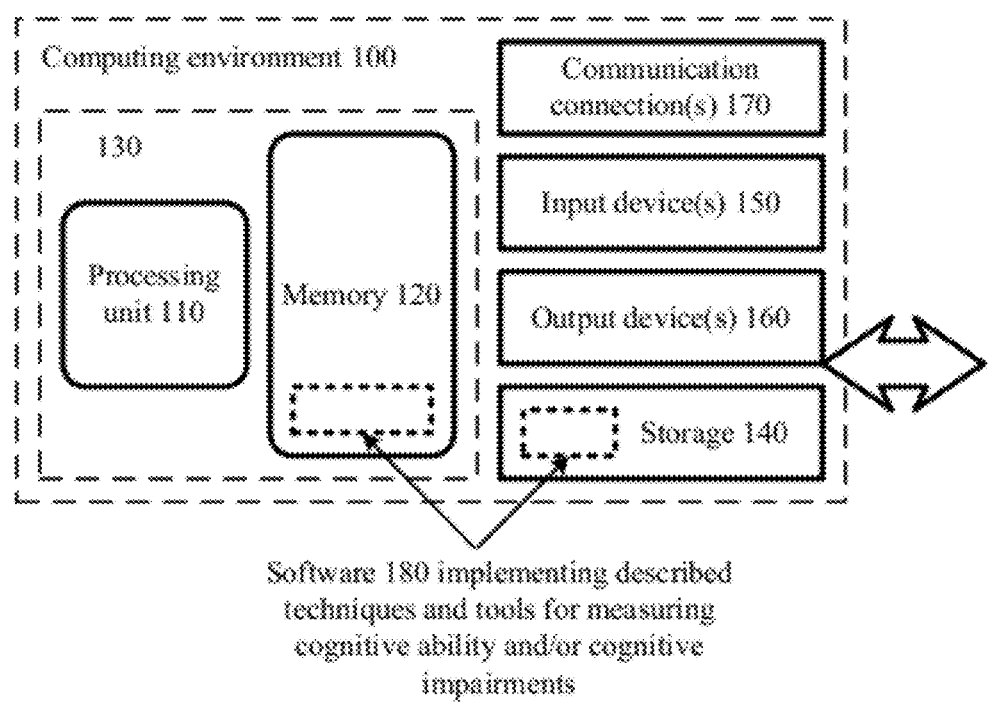
FIG. 1 is a block diagram of a suitable computing environment in conjunction with which several described embodiments may be implemented.

Described embodiments are directed to techniques and tools for measuring cognitive ability and/or detecting cognitive impairment or decline. For example, techniques and tools are described that can be used to diagnose or test susceptibility to cognitive impairments in children or in elderly people (such as cognitive impairments associated with Alzheimer's Disease). Techniques and tools are described that can be used to evaluate treatment effects and/or measure cognitive decline over time. The various techniques and tools described herein may be used independently. Some of the described techniques and tools can be used in combination.

The following paragraphs include a discussion of terms used herein.

"Adjusting for effects of X" refers to adjusting an interpreted result such that the condition X does not skew the interpreted result.

"Age-related cognitive decline" refers to a reduction in cognition associated with advancing age, e.g., an age-related dementia.

"Artificial intelligence" refers to information processing performed by one or more computers that mimics human reasoning.

"Based at least in part on X" means based on X and zero or more other acts, results, or conditions.

"Cognitive status" refers to status of cognition—mental processes related to knowing, thinking, learning and/or judging.

"First-person" refers to a simulation of a perspective a user would have if the user were physically present in a virtual environment.

"Learning of navigation skills" refers to gradual improvement of navigation skills through repetition, such as navigation skills used in a virtual reality environment.

"Learning of landscape" refers to gradual improvement of knowledge of a landscape, such as a landscape in a virtual reality environment.

"Measuring neural activity" refers to detecting activated brain regions. For example, neural activity can be measured using functional magnetic resonance imaging ("fMRI") techniques that measure changes in neuroanatomical activity, such as increased blood flow to areas of the brain having corresponding neurological functions.

"No change score" refers to a performance signifier that measures performance of a user in identifying situations with no change in image content or image location for a second set of one or more images relative to a first set of one or more images.

"Novel image" refers to a new image in a second set of one or more images relative to a first set of one or more images.

"Novel location" refers to a new location of an image in a second set of one or more images relative to a first set of one or more images.

"Pattern recognition" refers to identification of a pattern in data and association of the identified pattern with a condition or other data.

"Pediatric cognitive disability" refers to diminished cognition (as compared to unaffected normal peers) in a human child under the age of 18. Pediatric cognitive disability can be associated with, for example, a genetic abnormality or a neuropsychological disturbance.

"Pre-clinical Alzheimer's disease" refers to Alzheimer's disease in its early stages before memory disturbance significantly interferes with psychosocial function to an extent that a clinical diagnosis can be made based on the memory disturbance.

"Providing a treatment regimen" refers to setting or adjusting a treatment regimen, such as a dose of an anti-Alzheimer's disease medication or the degree to which an environment is structured to address the effects of dementia.

"Score" refers to a performance signifier, such as a number or percentage of successful trials.

"User" refers to a human being that uses or interacts with computer software and/or a computerized system.

"Virtual reality environment" refers to an environment that simulates a physical environment. For example, a computer can display a virtual reality environment to a user via a graphical display, and the user can interact with the virtual reality environment by transmitting input to the computer.

I. COMPUTING ENVIRONMENT

FIG. 1 illustrates a generalized example of a suitable computing environment (100) in which several of the described embodiments may be implemented. The computing environment (100) is not intended to suggest any limitation as to scope of use or functionality, as the techniques and tools may be implemented in diverse general-purpose or special-purpose computing environments.

With reference to FIG. 1, the computing environment (100) includes at least one processing unit (110) and memory (120). In FIG. 1, this most basic configuration (130) is included within a dashed line. The processing unit (110) executes computer-executable instructions and may be a real or a virtual processor. In a multi-processing system, multiple processing units execute computer-executable instructions to increase processing power. The memory (120) may be volatile memory (e.g., registers, cache, RAM), non-volatile memory (e.g., ROM, EEPROM, flash memory, etc.), or some combination of the two. The memory (120) stores software (180) implementing one or more of the described techniques and tools for testing cognitive ability and/or cognitive impairment.

A computing environment may have additional features. For example, the computing environment (100) includes storage (140), one or more input devices (150), one or more output devices (160), and one or more communication connections (170).

An interconnection mechanism (not shown) such as a bus, controller, or network interconnects the components of the computing environment (100). Typically, operating system software (not shown) provides an operating environment for other software executing in the computing environment (100), and coordinates activities of the components of the computing environment (100).

The storage (140) may be removable or non-removable, and includes magnetic disks, magnetic tapes or cassettes, CD-ROMs, DVDs, flash memory, or any other medium which can be used to store information and which can be accessed within the computing environment (100). The storage (140) stores instructions for the software (180).

The input device(s) (150) may be a touch input device such as a keyboard, mouse, pen, touch screen, or trackball, a voice input device, a scanning device, or another device that provides input to the computing environment (100). For audio or video encoding, the input device(s) (150) may be a sound card, video card, TV tuner card, or similar device that accepts audio or video input in analog or digital form, or a CD-ROM, CD-RW or DVD that reads audio or video samples into the computing environment (100). The output device(s) (160) may be a display, printer, speaker, CD- or DVD-writer, or another device that provides output from the computing environment (100).

The communication connection(s) (170) enable communication over a communication medium to another computing entity. The communication medium conveys information such as computer-executable instructions, audio or video input or output, or other data in a modulated data signal. A modulated data signal is a signal that has one or more of its characteristics set or changed in such a manner as to encode information in the signal. By way of example, and not limitation, communication media include wired or wireless techniques implemented with an electrical, optical, RF, infrared, acoustic, or other carrier.

The techniques and tools can be described in the general context of computer-readable media. Computer-readable media are any available media that can be accessed within a computing environment. By way of example, and not limitation, with the computing environment (100), computer-readable media include memory (120), storage (140), communication media, and combinations of any of the above.

The techniques and tools can be described in the general context of computer-executable instructions, such as those included in program modules, being executed in a computing environment on one or more target real processors or virtual processors. Generally, program modules include routines, programs, libraries, objects, classes, components, data structures, etc. that perform particular tasks or implement particular abstract data types. The functionality of the program modules may be combined or split between program modules as desired in various embodiments. Computer-executable instructions for program modules may be executed within a local or distributed computing environment.

II. GENERALIZED TECHNIQUE FOR ANALYSIS OF COGNITIVE STATUS USING VR TESTING

Figure 2:
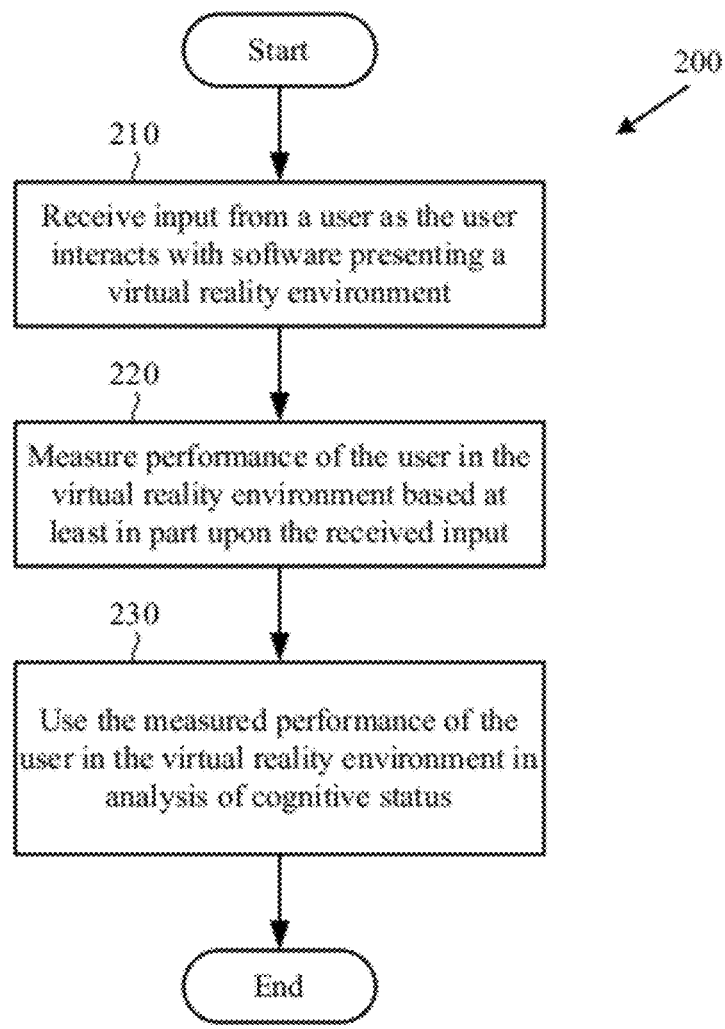
FIG. 2 is a flowchart of a generalized technique for analysis of cognitive status using VR testing.

FIG. 2 shows a generalized technique (200) for analysis of cognitive status of a user using testing with a virtual reality ("VR") environment. A software tool such as one operating in the computer system environment shown in FIG. 1 or other tool performs the technique. Example use scenarios and example clinical applications for the generalized technique (200) are described below.

The tool receives (210) input from the user as the user interacts with software presenting a VR environment. In example implementations (including those described in the following sections), the VR environment includes a first-person, three-dimensional graphical rendering of the environment as well as sound cues for the environment. The environment is graphically rendered on a computer monitor or, for a more immersive experience, presented to the user using virtual reality goggles or another head mounted display. Inputs (such as direction of movement, speed of movement) are received from the user using a force-feedback joystick, other joystick, mouse, keyboard or other input device.

Returning to FIG. 2, the tool measures (220) performance of the user in the VR environment based at least in part upon the received input. The organization of the VR environment depends on implementation but typically includes areas such as quadrants which may be organized in terms of a coordinate space. As an intermediate part of measuring performance, for example, the tool tracks position of the user over time in the coordinate space. The results of the tracking are stored in memory or a file (e.g., as timestamped coordinate locations) for later analysis of patterns of user behavior.

In terms of metrics, the tool measures one or more of the following: (1) distance (e.g., cumulative or start to target) traversed in the VR environment, (2) time elapsed before reaching a target (or targets) in the VR environment, (3) percentage of successful trials (where success is, e.g., finding a target), (4) time spent in a target area of the VR environment, (5) velocity of movement in the VR environment, (6) pattern of movement (e.g., between multiple areas or in terms of coordinates) in the VR environment, and/or (7) pattern of time spent in respective areas of the VR environment. Alternatively, the tool measures performance using other and/or additional metrics. Some metrics (such as velocity of movement and time elapsed before reaching a target) may depend on each other to some extent, while other metrics do not.

In some implementations, the tool measures performance in a series of VR tests, with some tests having one or more "visible" targets and other tests having one or more "hidden" targets. In the "visible" target trials, one or more visual or audible cues assist the user in finding a target. For example, a prominent flag or other graphical cue is placed next to the target to help the user find the target, or directional arrows guide the user to the target. In the hidden target trials, the performance of the user in finding the target(s) is measured without giving the user the cues from the visible target testing. Such tests help measure memory retention of the user in navigating the VR environment.

Returning to FIG. 2, the tool uses (230) the measured performance of the user in the VR environment in analysis of cognitive status. For example, the tool assesses: (a) the presence or extent of age-related cognitive decline (e.g., a decline in memory performance or learning performance), (b) presence or extent of pediatric cognitive disability (e.g., a memory performance problem or learning performance problem), (c) presence or extent of progression of Alzheimer's disease, (d) presence of a characteristic of pre-clinical Alzheimer's disease, and/or (e) response of the user to therapeutic intervention to treat cognitive decline. To make the assessment, the tool can use artificial intelligence mechanisms such as classifiers (e.g., neural networks) for pattern recognition, statistical analysis, etc. Example therapeutic interventions are presented below. Alternatively, the tool uses the measured performance for a different type of analysis.

The cognitive status assessment relates the measured performance to a cognitive status classification. In making the assessment, the tool can compensate for the effects of sex, age and/or learning about the VR environment (e.g., navigation skills, landscape) on the measured performance. The following sections describe observed correlations between sex, age and learning in example uses of the generalized technique (200), and such correlations can be compensated for during the assessment of cognitive status.

In some implementations, the user repeatedly takes the VR navigation test and the performance of the user over time is measured so as to assess changes in cognitive status of the user. Typically, this involves comparing cognitive status assessments from trial to trial for the user. In other implementations, the results of testing are compared for multiple users, e.g., as part of population studies for the efficacy of a therapy.

III. GENERALIZED TECHNIQUE FOR ANALYSIS OF COGNITIVE STATUS USING NINL TESTING

Figure 3:
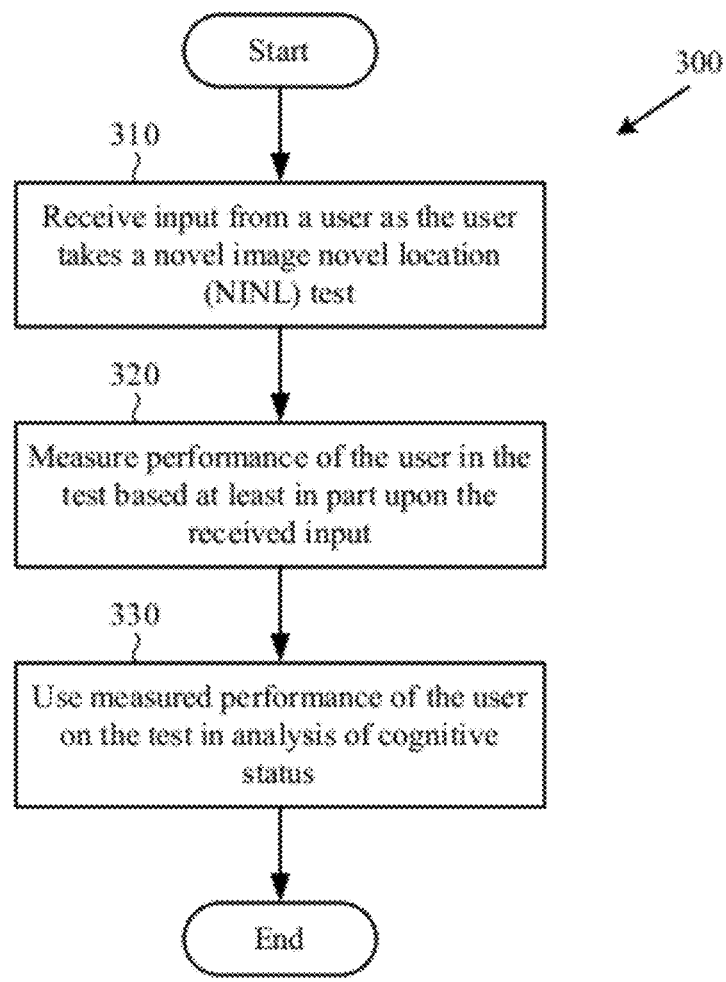
FIG. 3 is a flowchart of a generalized technique for analysis of cognitive status using Novel Image Novel Location ("NINL") testing.

FIG. 3 shows a generalized technique (300) for using measured performance of a user on a Novel Image Novel Location ("NINL") test in analysis of cognitive status. A software tool such as one operating in the computer system environment shown in FIG. 1 or other tool performs the technique. Alternatively, the NINL test is administered by a human supervisor using paper materials. Example use scenarios and example clinical applications for the generalized technique (300) are described below.

The tool receives (310) input from the user as the user takes the NINL test. In example implementations, a software tool graphically presents the NINL test to the user on a computer monitor as a series of images in panels or a slideshow. The software tool accepts input from the user via a keyboard, touchpad or mouse, or the software tool receives and process voice input from the user, or the software tool receives and processes another kind of input. In a typical NINL test, the input indicates whether the user perceives "no change" in an image or group of images presented to the user, a "new location" in the image(s), or a "new image" in the image(s). Alternatively, the choices presented to the user and/or selections received from the user have a different format.

Returning to FIG. 3, the tool measures (320) performance of the user in the NINL test based at least in part upon the received input. In some implementations, as described in the following sections, the tool presents a first set of images organized by location to the user. For example, the first set of images includes multiple panels with each panel including multiple images. The tool then presents a second set of images organized by location to the user. For example, the second set of images includes multiple panels with each panel including multiple images. To measure whether the user detects changes in image content and/or location, one or more images of the second set of images differs in image content and/or image location relative to the first set of images. Alternatively, the sets of images for the NINL test have a different configuration.

In terms of metrics, the tool measures one or more of the following: (1) a novel location score indicating performance of the user in identifying changes in locations of images; (2) a novel image score indicating performance of the user in identifying new images in a second set of one or more images relative to a first set of one or more images; and/or (3) a no change score indicating performance of the user in identifying situations with no change in image content or image location for a second set of one or more images relative to a first set of one or more images. Alternatively, the tool measures performance using other and/or additional metrics.

In some implementations, the tool measures performance in an "immediate" NINL test and also measures performance in a "delayed" NINL test. For example, the immediate NINL test occurs shortly after the user reviews a training set of images for the NINL test, and the delayed NINL test occurs some defined period (e.g., five minutes) after the immediate NINL test. The duration of the defined delay period depends on implementation and is set to measure memory retention performance of the user.

Returning to FIG. 3, the tool uses (330) the measured performance of the user on the test in analysis of cognitive status. For example, the tool assesses: (a) the presence or extent of age-related cognitive decline (e.g., a decline in memory performance or learning performance), (b) presence or extent of pediatric cognitive disability (e.g., a memory performance problem or learning performance problem), (c) presence or extent of progression of Alzheimer's disease, (d) presence of a characteristic of pre-clinical Alzheimer's disease, and/or (e) response of the user to therapeutic intervention to treat cognitive decline. Example therapeutic interventions are presented below. Alternatively, the tool assesses cognitive status for a different type of cognitive assessment.

The cognitive status assessment relates the measured performance to a cognitive status classification. In making the assessment, the tool can compensate for the effects of sex, age and/or learning about the testing on the measured performance. The following sections describe observed correlations between sex, age and learning in example uses of the generalized technique (300), and such correlations can be compensated for during the assessment of cognitive status.

In some implementations, the user repeatedly takes the NINL test and the performance of the user over time is measured so as to assess changes in cognitive status of the user. Typically, this involves comparing cognitive status assessments from trial to trial for the user. In other implementations, the results of testing are compared for multiple users, e.g., as part of population studies for the efficacy of a therapy.

IV. EXAMPLE USE SCENARIOS

The generalized techniques (200, 300) can be used in various scenarios, including but not limited to home use scenarios, professional use scenarios with fMRI equipment, professional use scenarios with MRI equipment, and professional use scenarios with just the testing.

For example, when used with MRI equipment (or fMRI equipment), the equipment measures neural activity of the user as the user takes the NINL test and/or VR test. A cognitive status assessment for the user can then also be based on the measured neural activity.

Or, when used in a home use scenario, the user takes the NINL test and/or the VR test on a home computer system such as a desktop or laptop computer. The test can be delivered to the user on a computer-readable medium such as a disk or delivered to the user over a network connection from a server computer system. The user inputs can be received and processed locally to measure performance and assess cognitive status, or information can be forwarded to a remote server computer site to measure performance and/or assess cognitive status.

Alternatively, the NINL testing and/or VR testing is performed in conjunction with other and/or additional batteries of cognitive tests or physical evaluations of the user.

Described implementations can be used in a variety of contexts, such as psychological testing or clinical trials involving children and/or the elderly. The NINL object recognition test and the Memory Island spatial navigation test turned out to be sensitive to detect differences in learning and memory performance in these two populations. The sensitivity of these tests is a potential benefit or advantage over other technology. For example, in contrast to established cognitive tests, these tests were shown to be sensitive to effects of APOE $\epsilon4$ (a risk factor for developing Alzheimer's disease and cognitive impairments following various environmental challenges) in non-demented elderly and children. Other advantages and problems to be solved are presented herein.

V. EXAMPLE THERAPEUTIC INTERVENTIONS

In example implementations, cognitive status assessments are used to make decisions about therapeutic interventions for users (e.g., children or elderly). In general, in this context, a therapeutic intervention is a known or proposed treatment for cognitive decline, such as the cognitive decline caused by normal aging or a pathological process, such as Alzheimer's disease or another condition associated with dementia, such as a neurological disease (for example, Huntington's Disease, Parkinson's disease, Creutzfeldt-Jakob Disease or a brain tumor), a vascular disorder (such as multi-infarct dementia or stroke), an infectious etiology (such as HIV/AIDS, spongiform encephalopathy, or syphilis), a toxic exposure (for example, to lead or alcohol), or an undesired effect of a drug. When the treatment is a proposed treatment, it can be administered as part of a clinical trial, and the response of the subject to the treatment can be assessed by the performance of the subject in the VR environment and/or NINL testing.

For example, the therapeutic intervention includes a drug therapy, and the cognitive status assessment is used in determining a therapeutic dose of the drug therapy. In the context of treating cognitive decline, for example, the therapeutic intervention is an APOE $\epsilon4$ inhibitor, an APOE $\epsilon3$ or APOE $\epsilon2$ mimetic, a cholinesterase inhibitor, an N-methyl-aspartate receptor antagonist, or a vitamin. Or, the therapeutic intervention includes hormone therapy using testosterone and/or another androgen, or using estrogen.

VI. EFFECTS OF SEX ON OBJECT RECOGNITION AND SPATIAL NAVIGATION IN HUMANS

This section describes example implementations of NINL tests and VR spatial navigation tests, then details results of performance on the tests in a first series of trials. It includes discussion of specific problems addressed and advantages for the example test implementations in some contexts. Alternatively, implementations of the NINL and VR spatial navigation techniques and tools vary in terms of technical details, specific advantages and/or problems solved.

A computer-generated VR island environment was developed to mirror the water maze paradigm of spatial learning and memory sensitive to effects of sex on age-related cognitive decline in mouse studies. The participants were trained to navigate to a visible target and subsequently to a hidden target. A joystick was used to control direction and speed of body movement. In addition, potential effects of sex on facial recognition and object recognition were tested using faces and NINL testing, respectively.

A. Materials and Methods

1. Participants

To determine the effects of sex on cognitive test performance, 27 community college students between 20 and 44 years of age (mean age±S.E.M., 30.3±1.2 years of age; 14 males (mean age±S.E.M., 29.1±1.4 years of age) and 13 females (mean age±S.E.M., 31.5±1.9 years of age)) were tested.

To determine whether use of a head-mounted display ("HMD") system (HMD model V8, Virtual Research System Inc., Santa Clara, Calif.) influences performance in a spatial learning and memory test requiring navigation (see below), 24 additional young participants between 17 and 40 years of age (mean age±S.E.M., 30.5±1.2 years of age; 14 males and 10 females) were recruited from the Oregon Health Science University campus community.

2. Facial Recognition

The testing began with two non-computerized memory tests. The first of these was a facial recognition test (Faces I and Faces II), a part of the Wechsler Memory Scale III developed and published by the Psychological Corporation. In this test, the participant was shown a series of 24 faces and asked to remember each one. Immediately after, the participant was shown another series of 48 faces (the 24 original faces plus 24 distracter faces) and asked to indicate whether each face was one of the faces they were directed to remember earlier or not (Faces I score). After an interval of five minutes, the participant was shown a different set of 48 faces (the same 24 original faces plus 24 new distracter faces) and again asked to indicate whether each face was one of the faces they were directed to remember earlier or not (Faces II score). For the Faces I and Faces II scores, the participant received one point for a correct response and zero points for an incorrect response with a maximal total of 48 points.

3. Object Recognition

Following the facial recognition test, an object recognition test entitled Novel Image, Novel Location ("NINL") test was presented to the study participants. In this test, the participant was presented with a series of 12 panels, one at a time, for eight seconds each. Each panel consisted of four quadrants (A, B, C, and D), with a different image in three of the four quadrants. The images were all similar in complexity but different in content. Positioning of the images within three of the four quadrants varied between panels.

Figure 4:
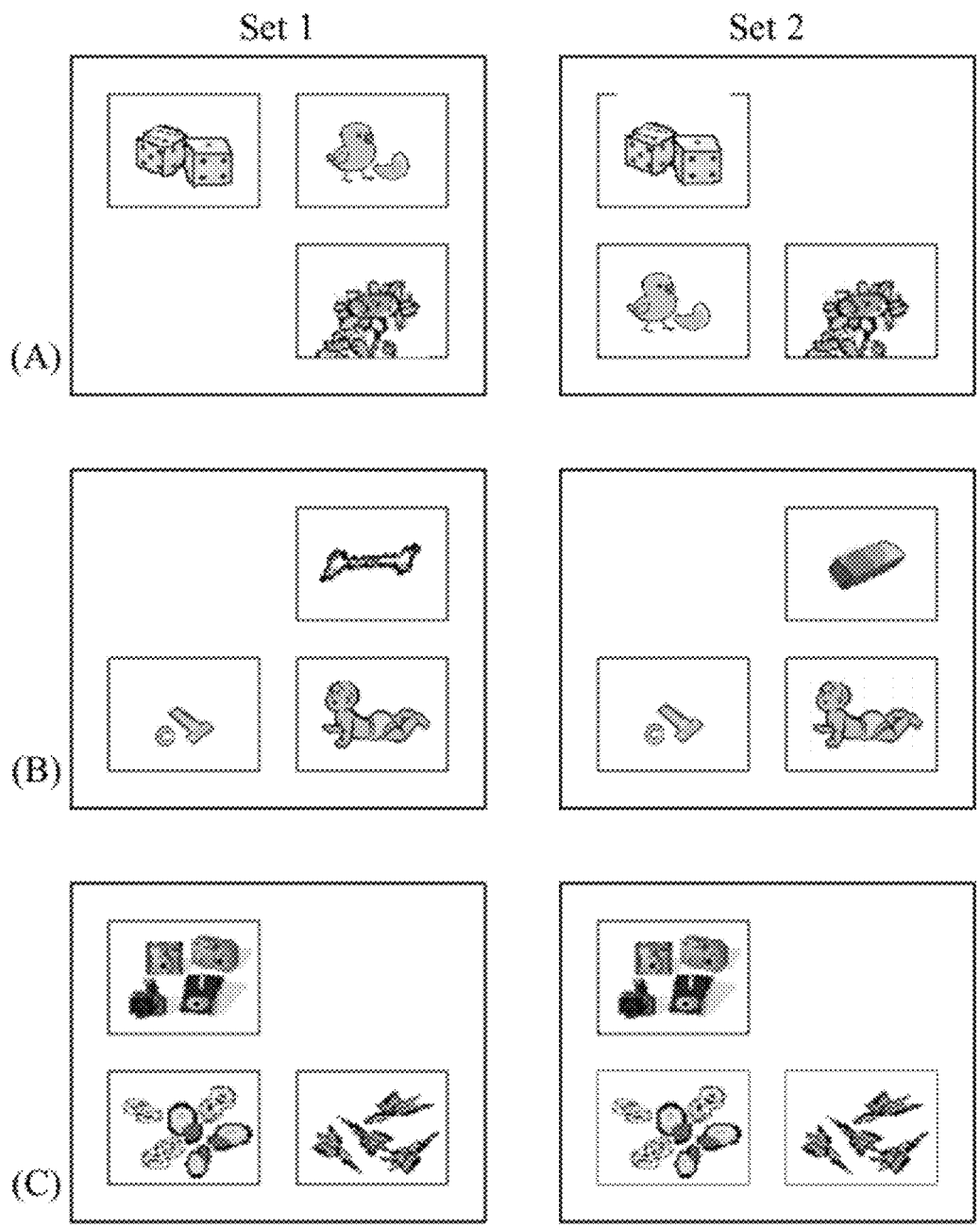
FIG. 4 is a diagram showing example panels of a NINL software tool according to one or more described embodiments.

FIG. 4 is a diagram showing example panels of the NINL software tool. On the left are panels from the first set. On the right are the corresponding panels from the second set, containing a novel location (A), novel image (B), or no change (C).

For each panel, the participant was asked to remember the images and their positions. After the participant had been presented the first set of 12 panels, they were immediately presented with a second set of 12 panels. After five minutes, they were again presented the second set of 12 panels. In the second set, the panels were either identical to, or slightly different from their counterparts in the first set. The variations in the new panels were either in the positioning of one of the three images (Novel Location) or in that they contained a novel image in the location previously containing one of the three familiar images (Novel Image). Out of the 12 panels in the second set, 4 panels were identical to panels shown in the first set, four panels contained a familiar image in a novel location, and four panels contained a novel image in place of a familiar image. For each of the 12 panels in the second set, the participant was asked to identify the new panel as being either identical to the corresponding panel in the first set ("Yes" answer), or containing a novel image or a novel location of a familiar image ("No" answer), with a maximum score of 12. These answers provided the total score.

Test performance was also analyzed with four sub-scores. If a panel was identified as containing a novel image, the participant was asked which image on the panel was novel. If a panel was identified as containing a novel location of a familiar image, the participant was asked the novel location of the familiar image on the panel. The "No Change" sub-score (four points max) reflected correct identification of panels identical to those seen in the first set. No points were deducted for incorrect identification of a panel as being identical to one seen in the first set. The "Change" sub-score (eight points max) reflected the ability to identify and characterize the type of anomaly in the panel (novel location or novel image), but not whether the particular image that changed was identified. No points were given when a change was indicated but the type of anomaly (novel location or novel image) was not correctly identified. The final two sub-scores reflected the ability to correctly identify the exact Novel Location (maximal four points) or Novel Image (maximal four points). In preliminary studies involving study participants age-matched to those in the current study, the version of the object recognition test described worked well and did not lead to a ceiling effect in test performance as a result of being too easy.

4. Memory Island

Next, a computer-generated virtual reality world (Memory Island) was used to assess spatial learning and memory. The participants were immersed in a computer-generated three-dimensional environment through a HMD system (HMD model V8, Virtual Research System Inc., Santa Clara, Calif.) comprised of special LCD video goggles and Sennheiser headphones. Inside the visor of the helmet were two video screens, one for each eye, generating a three-dimensional visual experience. Two earphones presented stereo sounds that coincided with the visual images in the visor, further enhancing the immersion experience. A Microsoft Sidewinder joystick determined the direction and speed of movement in the virtual world. As mentioned earlier, to determine whether use of the HMD influences performance in a spatial learning and memory test requiring navigation, an additional cohort of participants was tested with and without the HMD in two subsequent sessions using a counterbalanced design. Each session included four visible target trials, four hidden target trials (target only visible in very close proximity to the target), and a probe trial (no target present). Movement of the participant was tracked and recorded in time-stamped coordinate files, which were used to calculate speed of movement, time to reach the target (latency), and percentage time spent in each quadrant during the visible target session and hidden target session. Percentage time spent in each quadrant is a valuable measure, as it is usually independent of velocity.

The virtual world simulated an island environment of 347 m×287 m comprised of four quadrants. FIG. 5 is a diagram showing screen shots of the virtual reality, spatial navigation Memory Island software tool. A flag marks the location of the target during the visible target session (A) while no flag is present during the hidden target session (B). Each quadrant of the island has a different target. The target in quadrant 1 is a fountain (C), in quadrant 2 a piece of moving art (D), in quadrant 3 a seal (E), and in quadrant 4 a seagull (F).

As shown in FIG. 5, each quadrant contained a different target item. The participant was first asked to navigate to a target location visibly marked with a flag adjacent to the target (visible target). Targets in all four quadrants were used for visible target training in four consecutive trials. The starting orientation of the participant was varied in each trial, and these variations were kept consistent for all participants. As the starting orientation for a particular trial influenced the difficulty level of that trial, mean performance over the four trials of the visible or hidden target session were used for data analysis rather than performance during individual trials. After training to locate the visible targets, the participant was trained to navigate to a hidden target (here, no flag adjacent to the target, so the participant had to remember where the hidden target was and how to get there). The location of the hidden target was kept constant for each participant. Participants were given four trials with the hidden target. If the participant was unable to locate the target within two minutes, an arrow appeared to guide them to it. Trials in which the target was located within two minutes were defined as successful trials. The percentage of successful trials in the visible and hidden target session was used as an additional performance measure. Following the hidden target trials, the participant received a thirty second probe trial (target removed).

5. Statistical Analysis

Statistical differences between groups were determined by ANOVA, with sex as between participant factor, followed by Tukey-Kramer post hoc tests when appropriate. For analyzing probe trial data on Memory Island, the environment was divided into four quadrants and data was analyzed for the percentage of time spent in each quadrant, with the percentage of time spent in each quadrant as a within-participant measure. To assess significance of linear correlations, Pearson correlation calculations with two-tailed p values were used. All these statistics were performed using JMP software (SAS Institute Inc., Cary, N.C.).

B. Results of the First Series of Trials human tests designed to mirror rodent tests of object recognition and spatial navigation were administered to adult cognitively healthy humans. Facial recognition was also assessed. The trial results showed no statistically significant sex difference in facial recognition, consistent with earlier studies. In the object recognition test, the test-retest NINL total scores during the same visit were highly correlated, comparable to the test-retest correlations obtained in the established facial recognition test. No statistically significant effects were identified for sex on object recognition. However, in the spatial navigation test, effects were identified for sex on spatial learning and memory during the session with the hidden, but not visible, target. These tests are useful to compare assessments of object recognition and spatial learning and memory in humans and animal models.

1. Facial Recognition Scores

Figure 6:
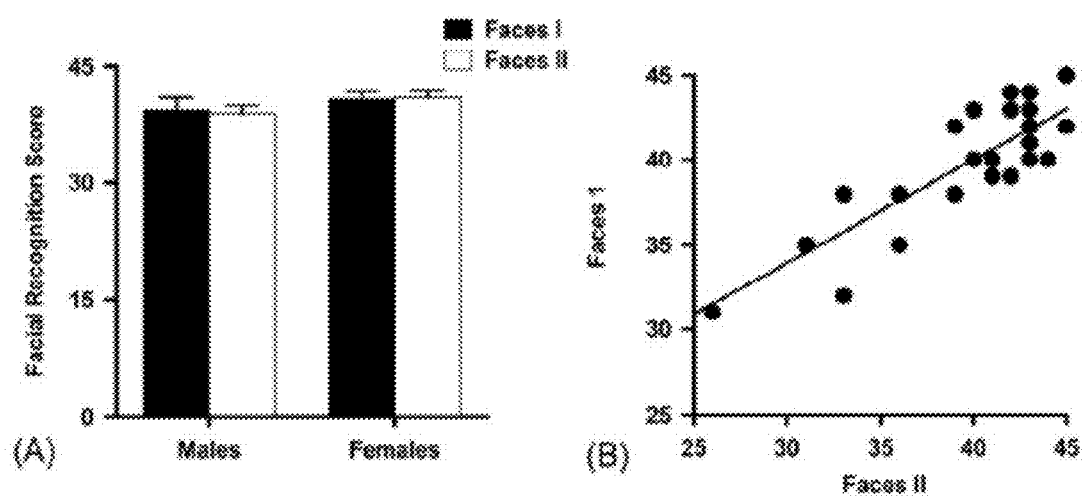
FIGS. 6A and 6B are charts showing comparable facial recognition scores in male and female participants, and correlation of the Faces I and Faces II scores, respectively.

First, facial recognition was assessed. FIGS. 6A and 6B are charts showing comparable facial recognition scores in male and female participants, and correlation of the Faces I and Faces II scores, respectively (n=14 males and n=13 females). No statistically significant effect was identified for sex ($F=0.5043$, $p=0.6810$, FIG. 6A) on facial recognition scores. The scores of Faces I and Faces II were highly correlated ($r=0.8182$, $p<0.0001$, FIG. 6B).

2. Novel Image and Novel Location (NINL)

Next, participants were tested for object recognition. FIGS. 7A-7F are charts showing (A) NINL total scores of male and female participants, (B) correlation of NINL I and NINL II, (C) scores indicating ability to detect a change, (D) scores indicating ability to detect a novel image, (E) scores indicating ability to detect a novel location of a familiar image, and (F) correlation of combined NINL total scores and combined facial recognition total scores, respectively (n=14 males and n=13 females).

Figure 7:
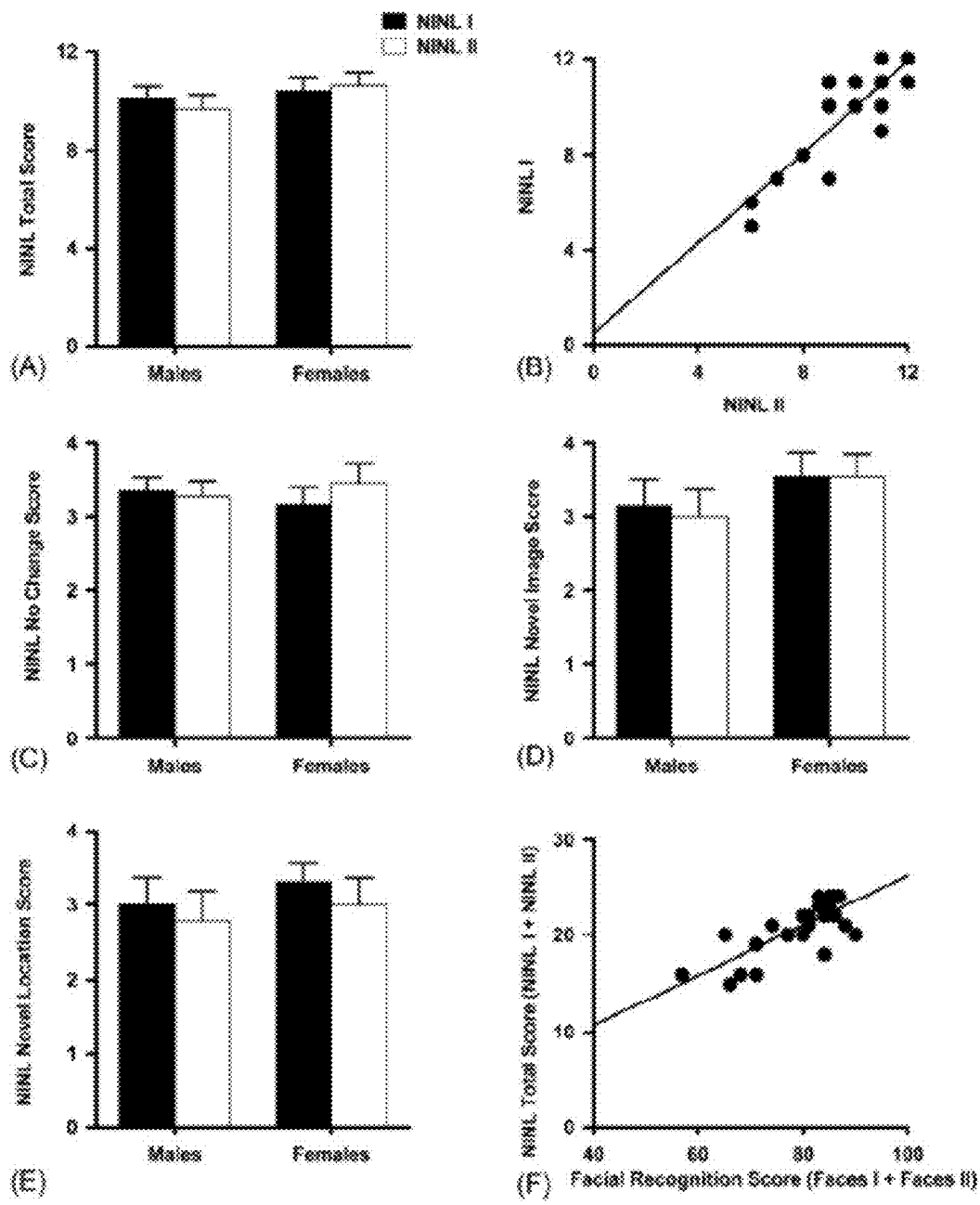
FIGS. 7A-7F are charts showing NINL total scores of male and female participants, correlation of NINL I and NINL II, NINL scores for ability to detect a change, NINL scores for ability to detect a novel image, NINL scores for ability to detect a novel location of a familiar image, and correlation of combined NINL total scores and combined facial recognition total scores, respectively, according to one or more described embodiments.

As with the facial recognition test, no statistically significant effect was identified for sex on NINL total scores ($F=0.5805$, $p=0.6305$, FIG. 7A). The scores of NINL trials 1 and 2 were highly correlated ($r=0.8775$, $p<0.0001$, FIG. 7B). Interestingly, the combined total scores for facial recognition and NINL total scores were also highly correlated ($r=0.5228$, $p<0.005$, FIG. 7F).

With regard to the sub-scores, male and female participants showed no difference in their ability to detect a change ($F=0.3183$, $p=0.8121$, FIG. 7C), a novel image ($F=0.6360$, $p=0.5952$, FIG. 7D) or novel location ($F=0.4148$, $p=0.7431$, FIG. 7E).

3. Spatial Learning and Memory Requiring Navigation (Memory Island)

Figure 8:
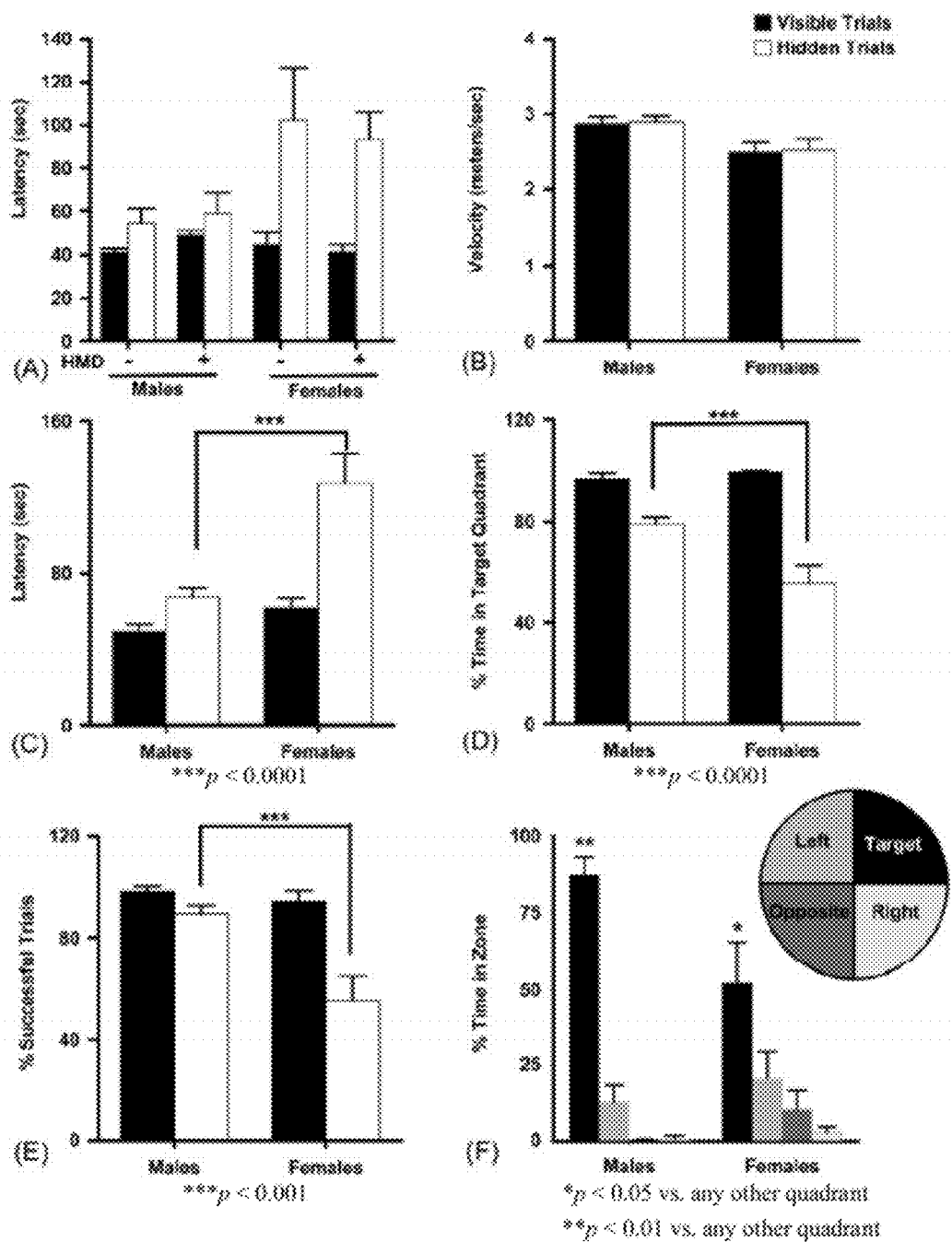
FIGS. 8A-8E are charts showing, for males and females tested with a virtual reality, spatial navigation software tool in hidden target trials and visible target trials, results for latency to reach the target with (+) or without (−) wearing a head-mounted display ("HMD"), velocity, latency to reach the target, percentage time in the target quadrant, percentage of successful trials, respectively, according to one or more described embodiments.
FIG. 8F is a chart showing, for males and females in a probe trial, percentage time in four quadrants, according to one or more described embodiments.

Finally, spatial learning and memory requiring navigation were assessed on Memory Island. FIGS. 8A-8E are charts showing, for males and females tested with a virtual reality, spatial navigation software tool in hidden target and visible target trials, (A) results for latency to reach the target with (+) or without (−) wearing a HMD, (B) velocity, (C) latency to reach the target, (D) percentage time in the target quadrant, (E) percentage of successful trials, respectively. FIG. 8F is a chart showing, for males and females in a probe trial, percentage time in four quadrants. In FIG. 8A, n=14 males and n=10 females for (A). In FIGS. 8B-8F, n=14 males and n=13 females.

The participants were first trained to locate a visible target in four trials (visible target session). Subsequently, they were trained to locate a hidden target in four trials (hidden target session). No statistically significant effect was identified for the use of the HMD to perform this task on time to locate the target (latency) ($F=0.92$, $p=0.5150$, FIG. 8A), velocity ($F=1.24$, $p=0.5300$, FIG. 8B) or percentage time spent in the target quadrant ($F=2.14$, $p=0.323$, FIG. 8D) during the visible or hidden target session.

In both the visible target session and the hidden target session, the female participants moved slower (lower velocities) ($F=15.59$, $p<0.0002$, FIG. 8B) than the male participants. Analyzing the visible and hidden target sessions combined by repeated measures, the female participants showed higher latencies ($F=19.22$, $p<0.0001$, FIG. 8C) than the male participants and there was a sex×session interaction ($F=7.80$, $p=0.008$). In the hidden target session, but not the visible target session, the females showed higher latencies than the males (FIG. 8C). As the female participants moved slower than the male participants in both the visible and hidden target session and the magnitude of this sex difference was comparable in the visible and the hidden target session (FIG. 8B), the sex difference in moving speeds did not account for the sex difference in latencies in the hidden target session (FIG. 8C).

Percentage time in the target quadrant, which is typically not affected by velocity, was also measured. In the visible target session, female and male participants had no difficulty in locating the target and spent close to 100% of their time searching in the target quadrant (FIG. 8D). In contrast, in the hidden target session, female participants spent less time in the target quadrant than male participants (F=12.27, p<0.001).

Additionally, the percentage of "successful" trials for each participant was measured (FIG. 8E). A successful trial was defined as a trial in which the target was located within 120 seconds. Female participants had fewer successful trials than male participants in the hidden target session (F=10.29, p=0.0021), but not the visible target session (F=1.94, p=0.2652).

Following the hidden target session, the participants performed a 30-second probe trial in which there was no target present. The participants were unaware of the absence of the target during the probe trial, and were asked to perform one last trial with the hidden target. Both females and males spent most of their time searching in the target quadrant (FIG. 8F). There was a trend towards a sex difference with the males spending more time in the target quadrant than the females, but that did not reach significance (F=3.49, p=0.0715).

4. Sex and Performance

Figure 9:
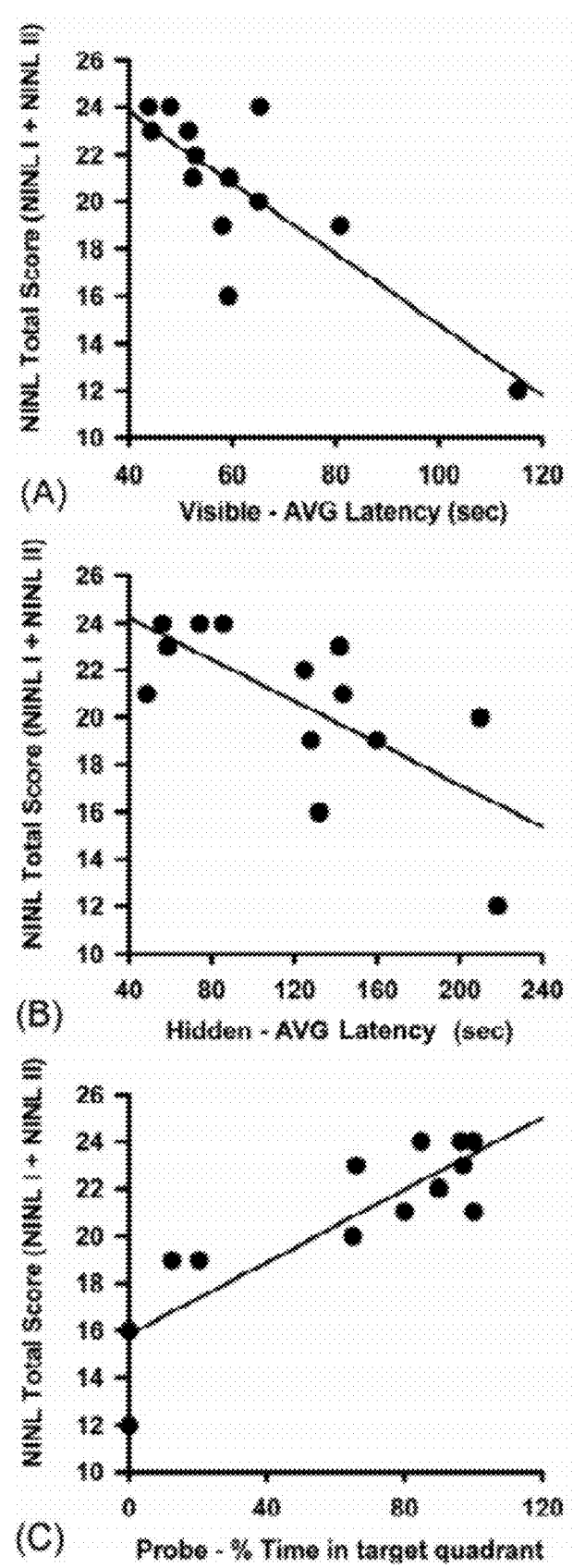
FIGS. 9A-9C are charts showing correlation between NINL total scores and latency to reach the target during a visible target session with a virtual reality, spatial navigation software tool, correlation between NINL total scores and latency to reach the target during a hidden target session with a virtual reality, spatial navigation software tool, and correlation between NINL total scores and percentage of time spent in the target quadrant during a probe trial, respectively, according to one or more described embodiments.

Since there were sex differences in spatial navigation measures on Memory Island, these measures were examined for correlation with performance on the other behavioral tests. FIGS. 9A-9C are charts showing correlation between NINL total scores and latency to reach the target during a visible target session with a virtual reality, spatial navigation software tool, correlation between NINL total scores and latency to reach the target during a hidden target session with a virtual reality, spatial navigation software tool, and correlation between NINL total scores and percentage of time spent in the target quadrant during a probe trial, respectively.

In female, but not male, participants the combined NINL total scores correlated with average time to reach the target during the visible target session of Memory Island (r=−0.6736, p<0.01, FIG. 9A), with average time to reach the target during the hidden target session of Memory Island (r=−0.6005, p<0.03, FIG. 9B), and with percentage of time spent in the target quadrant in the probe trial (r=0.7217, p<0.01, FIG. 9C).

D. Discussion

In the object recognition test, the test-retest NINL total scores during the same visit were highly correlated, comparable to the test-retest correlations obtained in the established facial recognition test. In the spatial navigation test, effects were identified for sex on spatial learning and memory during the session with the hidden, but not visible, target. No statistically significant effects were identified for sex on object recognition.

There was a sex difference in the percentage of time in the target quadrant during the hidden target, but not visible target, session. This measure is independent of velocity and not biased by start location, as all participants started out in the center of the island. Therefore, these data tend to show a sex difference in ability to locate the hidden target per se, rather than in general ability to perform this task regardless of whether the target was visible or hidden.

The identified sex differences in spatial learning and memory on Memory Island are consistent with sex differences in visual spatial perception and in spatial learning and memory in real and other virtual environment navigation tasks. Functional magnetic resonance imaging ("fMRI") during navigational tasks has shown that women recruit the right parietal and right prefrontal area, whereas men recruit the left hippocampal area, which may relate to the predominant use of landmark cues by women and geometric and landmark cues by men. However, it might be more complex. The Memory Island test environment contains landmarks predicting the target location and still showed sex differences in performance. These data tend to show that the sex differences in spatial memory do not require the exclusion of stable landmarks.

The Memory Island test can be distinguished from prior studies that have adapted the water maze test to study spatial learning and memory in humans using VR. Programs designed to mirror the water maze test in rodent studies might lack elements found in real world situations. Compared to the prior studies, Memory Island involves a higher degree of immersion into the virtual environment. For example, Memory Island also contains environmental sounds (e.g., birds). While not a water maze environment, the design and analysis of the water maze test was incorporated into the design of Memory Island. Importantly, none of the participants experienced nausea or dizziness on Memory Island, while 10% of the participants experienced these symptoms after exposure to a virtual environment of interconnected hallways and other virtual environments in some prior studies.

In contrast to Memory Island, in NINL testing, no statistically significant effects were identified for sex on object recognition.

These tests are useful in comparing assessments of object recognition and spatial learning and memory in humans and animal models.

VII. EFFECTS OF SEX AND APOE $\epsilon$4 ON OBJECT RECOGNITION AND SPATIAL NAVIGATION IN THE ELDERLY After describing example implementations of NINL tests and VR spatial navigation tests, this section details results of performance on the tests in a second series of trials. It includes discussion of specific problems addressed and advantages for the example test implementations in some contexts. Alternatively, implementations of the NINL and VR spatial navigation techniques and tools vary in terms of technical details, specific advantages and/or problems solved.

In the second series of trials using example implementations of NINL tests and VR tests, to determine effects of APOE $\epsilon$4 ($\epsilon$4) on cognitive performance of healthy elderly, 115 non-demented elders (mean age 81 years) were cognitive tested. The established tests Faces, Family Pictures, Spatial Span Forward and Backward, as well as the object recognition and spatial navigation tests described herein, were used as cognitive tests. Salivary samples were collected to determine APOE genotype and salivary testosterone and cortisol levels.

Non-$\epsilon$4- and $\epsilon$4-carrying men and women did not differ in age, or Mini-Mental State Examination, Wide Range Achievement Test-Reading, Beck Anxiety Inventory, or reaction time scores. In the second series of trials, an effect was identified for $\epsilon$4 on the object recognition and spatial navigation tests, however, with non-$\epsilon$4 carriers outperforming $\epsilon$4 carriers, but not in the other cognitive tests. No relationship was found for sex and $\epsilon$4 status or sex and performance during the hidden target session of Memory Island. In men, salivary cortisol levels correlated with object recognition. These results show that object recognition and spatial navigation tests are useful to assess cognitive function in the elderly.

A. Procedures

1. Study Participants

To determine the effects of sex and $\epsilon$4 on cognitive performance in the non-demented elderly, people ranging in age from 62 to 92 (mean age±S.E.M., 81.60±0.57 years) were tested. The inclusion criteria were: 1) age 55 and over; and 2) stable medical conditions. Exclusion criteria were vision or hearing deficits severe enough to interfere with cognitive testing. Participants were given a Mini-Mental State Examination ("MMSE"), a short questionnaire that tests different areas of cognitive function, with a maximum score of 30. (See Kurlowicz et al., "The Mini Mental State Examination (MMSE)," *Try This: Best Practices in Nursing Care to Older Adults*, Hartford Institute for Geriatric Nursing, no. 3 (January 1999).)

All participants had MMSE scores equal or greater than 22 (see below).

The final sample was composed of 115 participants, all whites. The sample was divided into two APOE genotype groups, $\epsilon 4$ carriers and non-$\epsilon 4$ carriers. Those in the non-$\epsilon 4$ carriers group represented $\epsilon 3/\epsilon 3$ homozygotes and $\epsilon 2/\epsilon 3$ heterozygotes. Those in the $\epsilon 4$ carriers group represented $\epsilon 4/\epsilon 4$ homozygotes, $\epsilon 2/\epsilon 4$, and $\epsilon 3/\epsilon 4$ heterozygotes (Table 1).

TABLE 1

APOE genotype distribution of study participants. Values are presented as N (%) of women and men for each genotype.

| Genotype | Women | Men |
| --- | --- | --- |
| $\epsilon 2/\epsilon 3$ | 13 (15.1%) | 2 (6.9%) |
| $\epsilon 2/\epsilon 4$ | 1 (1.2%) | 0 (0.0%) |
| $\epsilon 3/\epsilon 3$ | 52 (59.3%) | 22 (75.9%) |
| $\epsilon 3/\epsilon 4$ | 18 (20.9) | 5 (17.2%) |
| $\epsilon 4/\epsilon 4$ | 2 (2.3%) | 0 (0.0%) |

The group of women consisted of 86 individuals (mean age±S.E.M., 81.2±0.7 years of age), among them 65 non-$\epsilon 4$ carriers and 21 $\epsilon 4$ carriers. The group of men consisted of 29 individuals (mean age±S.E.M., 82.9±0.9 years of age), among them 24 non-$\epsilon 4$ carriers and five $\epsilon 4$ carriers. There was no significant sex difference in the proportion of $\epsilon 4$ carriers among men and women. When cognitive status of the participants was assessed using the MMSE, 111 participants had a MMSE score greater than 23 which corresponds to a cutoff score for cognitively healthy people. The four participants who obtained a MMSE score below 24 (three scored 23, one scored 22) performed well on the other cognitive tests. As MMSE scores can be affected by other conditions such as hearing impairment, the data were analyzed with and without these four individuals included. Both analyses revealed a similar pattern of results. Therefore, these four participants were not excluded from the study.

Premorbid intellectual functioning general intelligence levels were evaluated using the Wide Range Achievement Test-Reading ("WRAT-R") instead of years of formal education. As anxiety levels and reaction times can influence performance on cognitive tests, they were analyzed as well. Levels of anxiety were assessed using the Beck Anxiety Inventory ("BAI"). Reaction_times were measured by presenting (on a computer screen) a series of colored ellipses at varying time intervals and asking the participants to press a button as soon as the ellipse appeared (Gary Darby, "Reaction Times," http://www.delphiforfun.org/Programs/Reaction_times.htm (©2000-2007)). The amount of time between the appearance of the stimulus and the time the button was pressed was recorded. No statistically significant differences were identified for age, cognitive status, pre-morbid intellectual functioning, anxiety levels or reaction times between men and women or non-$\epsilon 4$ and $\epsilon 4$-carrying study participants, respectively. (See Table 2.) The person testing the study participants was blinded to APOE genotype.

TABLE 2

Demography of study participants. Values are presented as N (%) or adjusted mean ± S.E.M., as indicated.

| Measure | Sex | | $\epsilon 4$ Status | |
| --- | --- | --- | --- | --- |
| | Women | Men | Non-$\epsilon 4$ | $\epsilon 4$ |
| Subjects [N (%)] | 86 (74.8%) | 29 (25.2%) | 89 (77.4%) | 26 (22.6%) |
| Mean age (years) | 81.2 ± 0.7 | 82.9 ± 0.9 | 81.9 ± 6.4 | 80.5 ± 1.2 |
| WRAT-R | 57.6 ± 1.0$^{a,b}$ | 57.5 ± 1.6$^c$ | 58.2 ± 1.0$^{a,c}$ | 55.3 ± 1.8$^b$ |
| MMSE | 27.3 ± 0.2 | 27.0 ± 0.3 | 27.3 ± 0.2 | 27.1 ± 0.4 |
| BAI | 4.2 ± 0.4$^{a,b}$ | 3.5 ± 0.8$^c$ | 4.2 ± 0.4$^{a,c}$ | 3.6 ± 0.7$^b$ |
| Reaction times$^d$ | 0.37 ± 0.01 | 0.40 ± 0.02 | 0.38 ± 0.01 | 0.39 ± 0.02 |

$^a$Two participants dropped out of the study between the two testing sessions.
$^b$Three participants dropped out of the study between the two testing sessions.
$^c$One score missing.
$^d$Two outliers removed from dataset.

2. Study Design

For APOE genotyping, samples of saliva were collected at the beginning of an evaluation session for a user. (See Table 3.)

TABLE 3

Sequence of cognitive testing.

| Test stage$^a$ | Description |
| --- | --- |
| 1 | Collection of a saliva sample$^b$ |
| 2 | Facial Recognition Immediate [Faces I] |
| | 5 min delay |
| | Face Recognition Delayed [Faces II] |
| 3 | NINL I |
| | 5 min delay |
| | NINL II |
| 4 | Reaction times |
| 5 | Memory Island: |
| | 3 Visible trials (three different targets: Seagull Art Piece Seal) |
| | 3 Hidden trials (Seagull Target) |
| | Probe trial |
| 6 | MMSE |
| 7 | FP I |
| | 5 min delay |
| | FP II |
| 8 | OraGene DNA Test$^c$ |

$^a$Three months following this session, additional tests such as BAI, the WAIS SSF and SSB, and the WRAT-R were conducted. These tests were not included in the first visit to minimize the length of the visit and potential fatigue.
$^b$Saliva samples were used to determine salivary cortisol and testosterone levels.
$^c$OraGene tests were used to determine APOE genotype.

The neuropsychological tests were administered in a designated apartment of the retirement community in two visits lasting around two hours and one hour, respectively. Table 3 illustrates the sequence of neuropsychological testing in both visits and the salivary collection. To control for circadian variations in hormone levels, all examinees were tested in the morning starting at 8:30 a.m.

3. Cognitive Tests a. Facial Recognition

For Faces I (immediate) and Faces II (delayed) tests (as in Section VI) to reduce the overall testing time and potential problems with fatigue, an interval of five minutes instead of 25 minutes was used between test and re-test for the facial recognition. A five-minute delay was also used for family pictures and object recognition tests. Performance on facial recognition was analyzed using Faces I and Faces II scores.

b. Family Pictures

Family Pictures I (FP I, immediate) and Family Pictures II (FP II, delayed) are also part of the Wechsler Memory Scale III developed and published by the Psychological Corporation. In the FP tests, the participants were asked to memorize as many details as they could from four different cartoon-like family scenes. After the four scenes were displayed for 10 seconds each, the examinees were prompted to describe which characters were in each scene, where they were positioned in the scene, and what they were doing. After an interval of five minutes, the study participants were asked the same question as in FP I. Each correct answer was scored as one point. Performance was analyzed using FP I and FP II scores.

c. Object Recognition

The example implementation of Novel Image Novel Location ("NINL") test described in Section VI was used in the second series of trials. Briefly, this example NINL test consists of two sets of three-image panels (12 panels in each set). The three pictures on each panel are similar in complexity but different in content and how they are randomly located in three of the four quadrants of the panel (A, B, C, and D). (See FIG. 1.) The first set of 12 panels is the reference set (here, the set participants are asked to memorize). The second set is the test set; panels are either identical to, or slightly different from, their counterparts in the first set. The variations in the second set of panels are either in the positioning of one of the three images or in that they contain a novel image instead of one of the three familiar images. Out of the 12 panels in the second set, four panels are identical to panels shown in the first set, four panels contain a familiar image in a novel location, and four panels contain a novel image in the original position of a familiar image.

The participants were first read the instructions and shown an example of what was expected from them in this test. Then they were presented with the first set of 12 panels (reference set), one at a time, for eight seconds each and asked to memorize the images and their positions. Without delay, they were presented with the second set of 12 panels and were prompted to identify each panel as being either identical to the corresponding panel in the first set ("No Change score"), or containing a novel image ("Novel Image score") or a novel location of a familiar image ("Novel Location score"). Their answers provided the total NINL immediate score, with a maximum of 12 points ("NINL I"). After five minutes (and without seeing the reference set again), participants were presented with the second set and asked the same questions. These answers provided the total NINL delayed score, with a maximum of 12 points ("NINL II"). Test performance was analyzed using NINL I, NINL II and three sub-scores for each. The Novel Location and Novel Image sub-scores reflected the ability to correctly identify the exact Novel Location and Novel Image, respectively (maximal four points each). The No Change sub-score reflected correct identification of panels identical to those seen in the first set (maximal four points).

d. Spatial Span Forward (SSF) and Spatial Span Backward (SSB)

SSF and SSB are also part of the Wechsler Memory Scale III developed and published by the Psychological Corporation. They provide a nonverbal measure of immediate memory. Both tests involve a board containing ten randomly anchored cubes. The participants were asked to watch the investigator tap the cubes (1 cube/second) in a prearranged order and to reproduce these tapping sequences. In the SSF test the tapping is performed in order of the example (forward), while in the SSB test it is performed in reverse order compared with the example (backward). The difficulty increases with the number of cubes tapped; from two cubes up to nine cubes. A correct sequence is scored as one point. Testing ended when the participants failed to reproduce the sequence correctly after two trials or when the pair of nine cubes sequence was tapped correctly.

e. Memory Island

Memory Island, a computer-generated virtual reality ("VR") world described in Section VI, was used in the second series of trials to assess spatial learning and memory requiring navigation. Briefly, the participants were immersed through a high quality 19-in. Dell computer monitor and a Harmon Kardon HK395 stereo speaker system with subwoofer. A Microsoft Sidewinder joystick was used to determine the direction and speed of movement in the virtual world. The virtual world simulated an island environment of $347 \times 287$ m$^2$ composed of four quadrants, each containing a different target item.

The participants were first asked to navigate to a target location visibly marked with a flag adjacent to the target (visible target session). Targets in all four quadrants were used for visible target training in three trials. The starting orientation of the participant was varied in each trial, and these variations were kept consistent for all participants, as the starting orientation for a particular trial influenced the difficulty level of that trial. After being trained to locate the visible targets, the participants were trained to navigate to a hidden target (here, no flag adjacent to the target) in three trials. In this part of the test, the participants had to remember where the hidden target was and how to get there (hidden target session). The location of the hidden target was kept constant for all participants (Seagull target). In each trial of the visible or hidden target session, if the participant was unable to locate the target within two minutes, a directional arrow appeared to guide them to the target. Following the hidden target trials, the participant performed a 30 second probe trial (target removed). In each trial, movement of the participants was tracked and recorded in time-stamped coordinate files, which were used to calculate total distance moved (feet), velocity (feet per second), latency (seconds), cumulative distance to the target (feet) and percentage time spent in the target quadrant until it was located or up to 120 seconds, whichever came first. For the probe trial, the percentage time spent in each quadrant was analyzed. Trials in which the target was located within two minutes were defined as successful trials. The percentage of successful trials in the visible and hidden target session was used as an additional measure of performance.

4. Salivary Cortisol and Testosterone

For assessment of salivary cortisol and testosterone levels and to assess potential correlations of these levels with measures of cognitive performance, samples of saliva were collected at the beginning of the session. (See Table 3.) Salivary cortisol and testosterone levels were determined using commercial kits by the General Clinical Research Center at Oregon Health Science University.

5. Statistical Analysis

As $\epsilon 2$ might provide protection against age-related cognitive decline, possible effects of $\epsilon 2$ on cognitive performance of the study participants were assessed. As no such effects were found, the study participants were divided in $\epsilon 4$ carriers and non-$\epsilon 4$ carriers. The lack of an effect of $\epsilon 2$ on cognitive performance of the study participants might have been caused by the relatively low number of $\epsilon 2$ carriers in this sample. Because performance on immediate and delayed parts of the cognitive tests from the same subjects is likely to be correlated, a mixed effects model (repeated measures design) was used to evaluate the change of cognitive performance test for recall parts (Family Pictures and Faces). This model was also adopted for analyzing performance across trials in Memory Island. Based on the Bayesian information criterion, a compound symmetrical structure as the variance-covariance matrix was selected.

In addition, generalized estimating equation ("GEE") regression for the object recognition outcomes, such as Novel Image, Novel Location, No Change, and Total NINL scores was used to obtain estimates clustered by study participant, and odds ratios were estimated for significant comparisons. The method of GEE is often used to analyze longitudinal and other correlated response data.

When tests did not contain a delayed recall part, statistical differences between $\epsilon 4$ and non-$\epsilon 4$-carrying groups as well as between men and women were determined using analyses of covariance ("ANCOVA") with, in both cases, age as a covariate. Regarding the probe trial, Mann-Whitney U tests were conducted to assess effects of sex and $\epsilon 4$ on time spent in the target quadrant. A Friedman test and when appropriate follow-up pairwise comparisons using Wilcoxon signed rank-tests were used to assess effects of sex and $\epsilon 4$ on the percentage of time spent in each quadrant of Memory Island. To assess significance of linear correlations, Pearson correlation calculations with two-tailed p-values were used. To limit the risk of violation of a normal distribution, outliers were removed from testosterone, cortisol and reaction times. Adjustment for multiple testing was handled by using repeated-measures analyses. Age was used as a covariate in all analyses.

Statistical analyses were performed using SPSS software (SPSS version 14.0: SPSS Inc., Chicago, Ill., USA) and Statistical Analysis System version 9.1 (SAS Institute, Cary, N.C., USA).

B. Results of Second Series of Trials

1. Facial Recognition

Performance was slightly better on Faces II than Faces I (F=6.91, p=0.010). The estimated mean for the Faces II was 35.70, while the estimated mean for the Faces I was 33.95 with a standard error of 0.53.

2. Family Pictures

Figure 10:
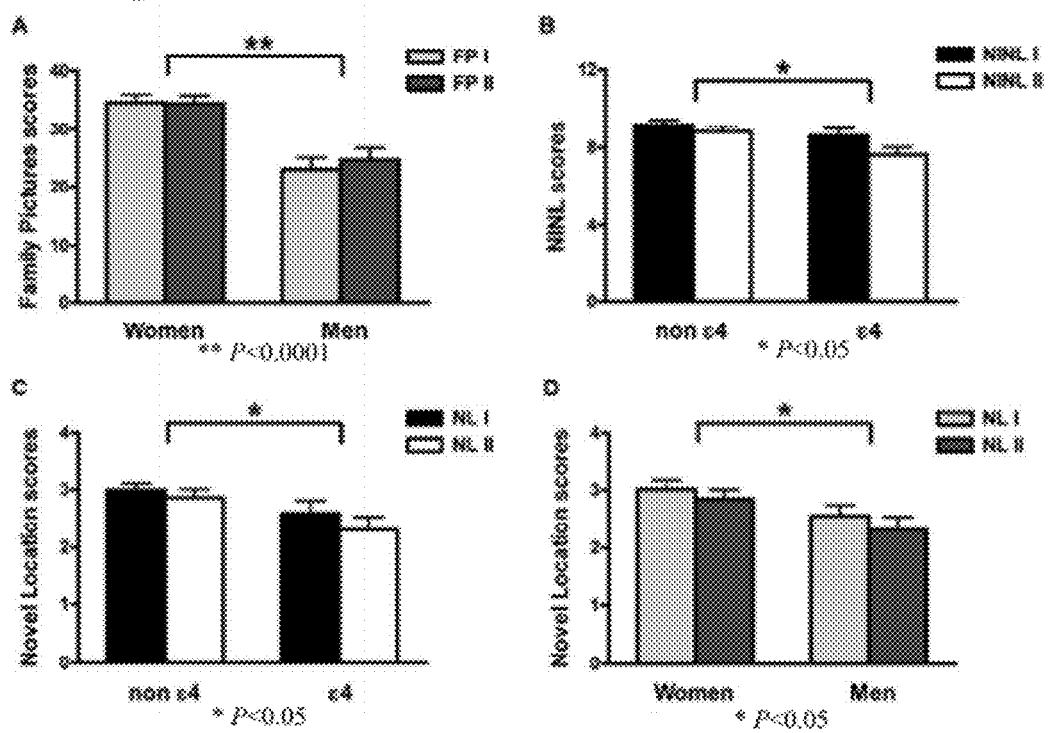
FIGS. 10A-10D are charts showing, for elderly women and men, an effect of sex on "Family Pictures" test scores, effect of APOE ε4 on NINL total scores (combined immediate and delayed scores), effect of APOE ε4 on Novel Location sub-scores (combined immediate and delayed scores), and effect of sex on Novel Location sub-scores, respectively, according to one or more described embodiments.

FIG. 10A is a chart showing, for elderly women and men, an effect of sex on "Family Pictures" test scores. There was strong evidence that women (estimated mean±S.E.M., 34.58±1.30) performed better than men (estimated mean±S.E.M., 23.84±2.09) in the Family Pictures test (F=22.52, p<0.001).

3. Object Recognition

FIG. 10B is a chart showing, for elderly women and men, an effect of $\epsilon 4$ on NINL total scores (combined immediate and delayed scores). An effect was identified for $\epsilon 4$ on NINL total scores (combined immediate and delayed scores) ($\chi^2=4.23$, p=0.040). At any given age, non-$\epsilon 4$ carriers had a higher estimated NINL total score than $\epsilon 4$ carriers. Mean NINL scores for non-$\epsilon 4$ and $\epsilon 4$ carriers were 9.01±0.25 and 8.10±0.39, respectively. There was a trial by $\epsilon 4$ interaction ($\chi^2=4.93$, p=0.026, FIG. 7B); comparing the immediate and delayed object recognition test total scores, $\epsilon 4$ carriers showed a larger decline in performance than non-$\epsilon 4$ carriers. With regard to the sub-scores, effects were identified for sex and $\epsilon 4$ on the novel location sub-scores (combined immediate and delayed scores). FIGS. 10C and 10D are charts showing, for elderly women and men, effect of $\epsilon 4$ on Novel Location sub-scores (combined immediate and delayed scores), and effect of sex on Novel Location sub-scores, respectively. There was suggestive evidence of non-$\epsilon 4$ carriers performing better than $\epsilon 4$ carriers ($\chi^2=4.01$, p=0.045, FIG. 10C) and of women performing better than men ($\chi^2=4.82$, p=0.028, FIG. 10D). For the no change sub-scores, interactive trial by $\epsilon 4$ effects were found ($\chi^2=7.64$, p=0.006). In contrast to the novel location sub-scores, the analyses of the novel image sub-scores yielded that performance was lower in the delayed score compared with the immediate recall ($\chi^2=5.30$, p=0.021).

4. Spatial Span

No statistically significant effects were identified for sex (F=1.21, p=0.273) or $\epsilon 4$ (F=0.79, p=0.375) on SSF test performance. SSB test performance showed no effects of $\epsilon 4$ (F=0.71, p=0.791), or effect of sex (F=1.60, p=0.209).

5. Memory Island

Figure 11:
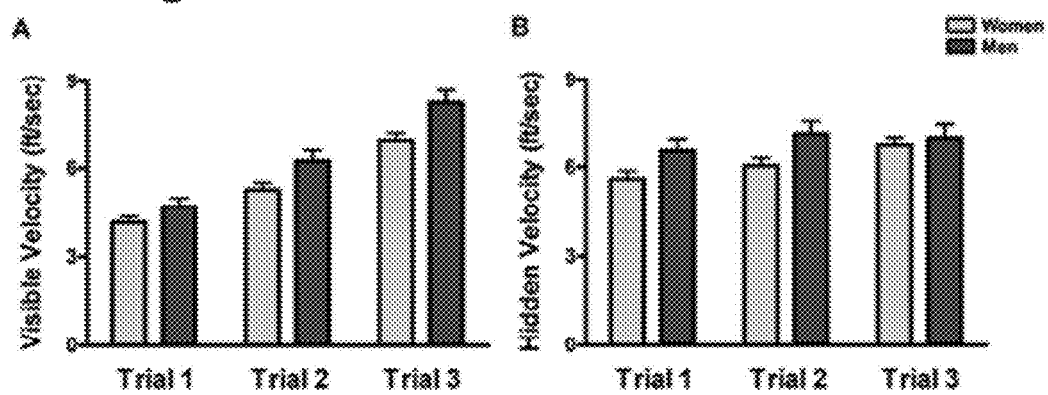
FIGS. 11A and 11B are charts showing, for elderly women and men tested with a virtual reality, spatial navigation software tool, effect of sex on velocity during visible target trials, and effect of sex on velocity during hidden target trials, respectively, according to one or more described embodiments.

Spatial learning and memory requiring navigation were assessed using a virtual reality, spatial navigation (Memory Island) test. FIGS. 11A and 11B are charts showing, for elderly women and men, effect of sex on velocity during visible target trials, and effect of sex on velocity during hidden target trials, respectively. FIGS. 12A-12F are charts showing, for elderly women and men, (A) effect of $\epsilon 4$ on velocity during a visible target session, (B) effect of $\epsilon 4$ on velocity during a hidden target session, (C) effect of $\epsilon 4$ on cumulative distance during a visible target session, (D) effect of $\epsilon 4$ on cumulative distance during a hidden target session, (E) effect of $\epsilon 4$ on latency to reach target during a visible target session, and (F) effect of $\epsilon 4$ on latency to reach target during a hidden target session (P<0.05), respectively.

Figure 12:
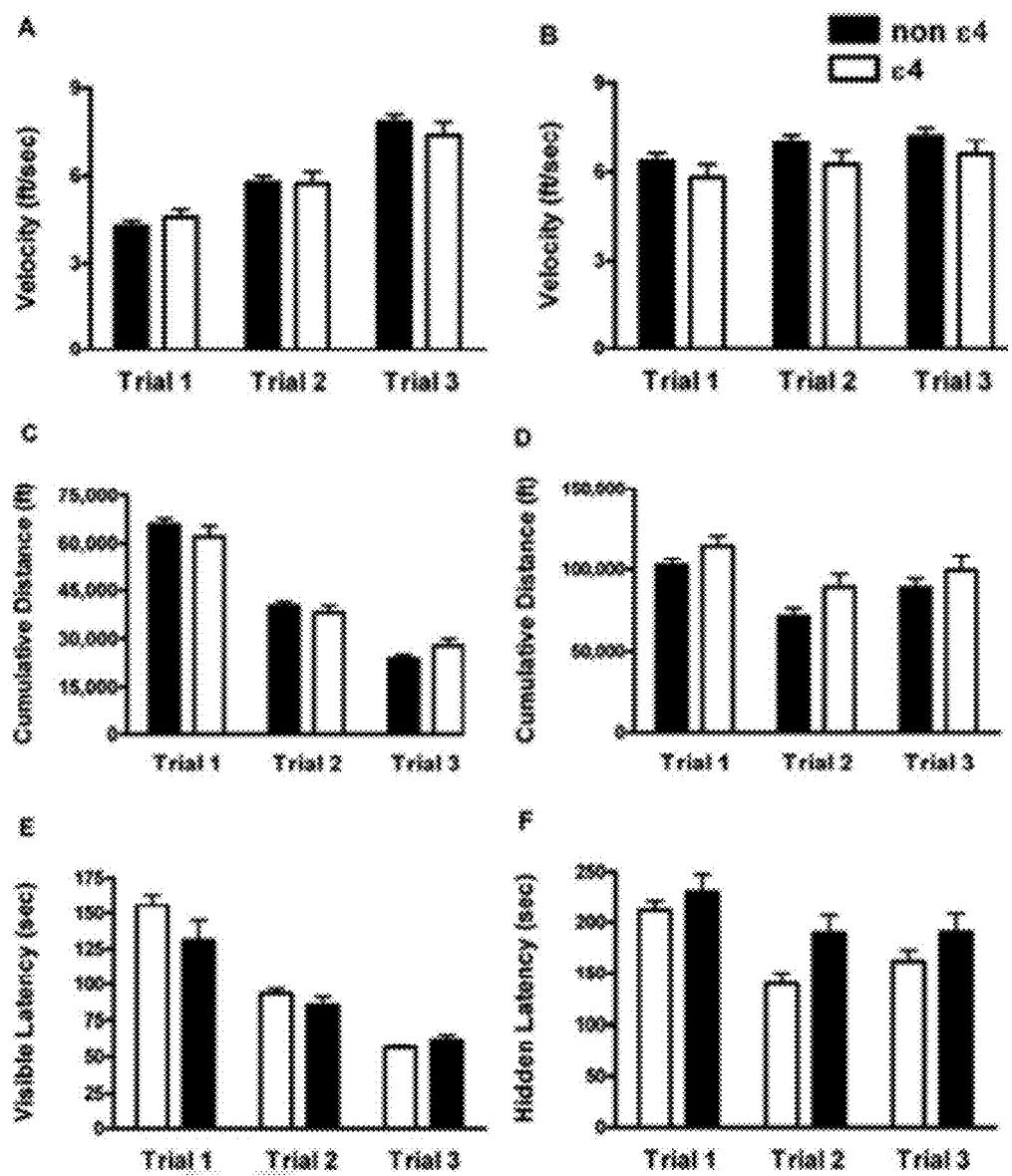
FIGS. 12A-12F are charts showing, for elderly women and men tested with a virtual reality, spatial navigation software tool, effect of APOE ε4 on velocity during a visible target session, effect of ε4 on velocity during a hidden target session, effect of APOE ε4 on cumulative distance during a visible target session, effect of APOE ε4 on cumulative distance during a hidden target session, effect of APOE ε4 on latency to reach target during a visible target session, and effect of APOE ε4 on latency to reach target during a hidden target session, respectively, according to one or more described embodiments.

During the visible target trials, an effect was identified for sex (F=8.15, p=0.005, FIG. 11A) on velocity. Therefore, average velocity during the visible target session was used as an additional covariate in all repeated-measures analyses of covariance (except for percentage time spent in the target quadrant as it is typically not related to speed of movement). Velocity also increased significantly across the visible trials (F=3.58, p=0.036). Learning curves during the visible trials (as shown in FIGS. 12A, 12B, 12C and 12D) demonstrate that the participants understood and could navigate in the three dimensional virtual environment. As shown in FIG. 12A, overall velocity increased across trials during the visible target session (P<0.05). During the hidden target session, effects of $\epsilon 4$ were found on cumulative distance to the target (F=5.14, p=0.026, FIG. 12D) and on latency (F=6.17, p=0.015, FIG. 12F). For example, $\epsilon 4$ carriers showed larger cumulative distance to the target at 120 seconds compared with non-$\epsilon 4$ carriers (P<0.05). In contrast, no statistically significant effects were identified for $\epsilon 4$ on cumulative distance (FIG. 12C) or latency to the target during the visible target session (FIG. 12E).

Figure 13:
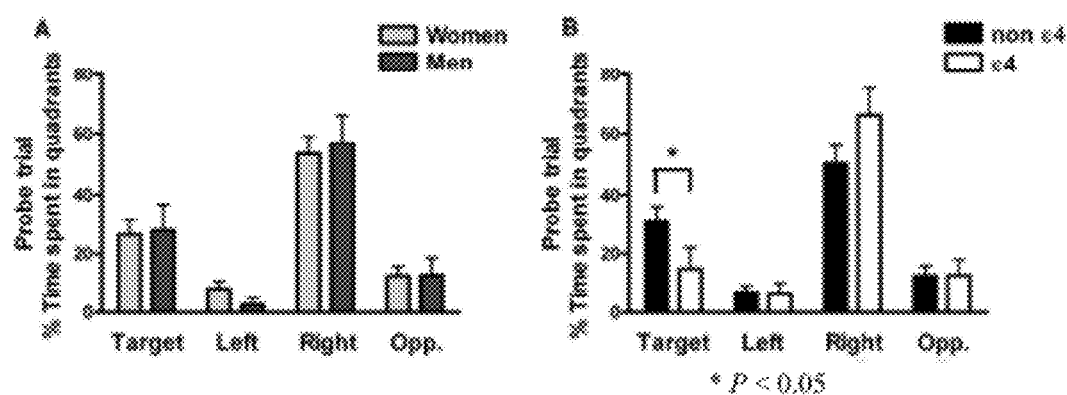
FIGS. 13A and 13B are charts showing, for elderly women and men tested with a virtual reality, spatial navigation software tool in a probe trial, effect of sex on percentage of time spent in four quadrants, and effect of APOE ε4 on percentage of time spent in four quadrants, respectively, according to one or more described embodiments.

FIGS. 13A and 13B are charts showing, for elderly women and men tested with a virtual reality, spatial navigation software tool in a probe trial (target removed), effect of sex on percentage of time spent in four quadrants, and effect of $\epsilon 4$ on percentage of time spent in four quadrants, respectively. Women spent more time in the right quadrant (P<0.01) compared with the target quadrant and more time in the target quadrant compared with the left (P<0.05) and to the opposite quadrant (P<0.01) while men spent more time in the target quadrant compared with the left quadrant (P<0.05). Non-$\epsilon 4$ carriers spent more time in the target compared with the left quadrant (P<0.001) and the opposite quadrant (P<0.05) while $\epsilon 4$ carriers spent more time in the right quadrant compared with the target quadrant (P<0.01).

In particular, women spent more time in the right quadrant than the target quadrant (z=−2.68, p=0.007), and more time in the target quadrant than the left (z=−2.92, p=0.004) and opposite quadrant (z=−2.07, p=0.039), while men spent only more time in the target quadrant than the left quadrant (z=−2.45, p=0.014) (FIG. 13A). Non-ε4 carriers spent more time in the target quadrant than the left (z=−3.59, p<0.001) and the opposite quadrant (z=−2.54, p=0.011) while ε4 carriers spent more time in the right quadrant than the target quadrant (z=−2.74, p=0.006, FIG. 13B). Comparatively, non-ε4 carriers spent more time in the target quadrant (31%) than ε4 carriers (15%) (z=−2.03, p=0.042, FIG. 13B).

Figure 14:
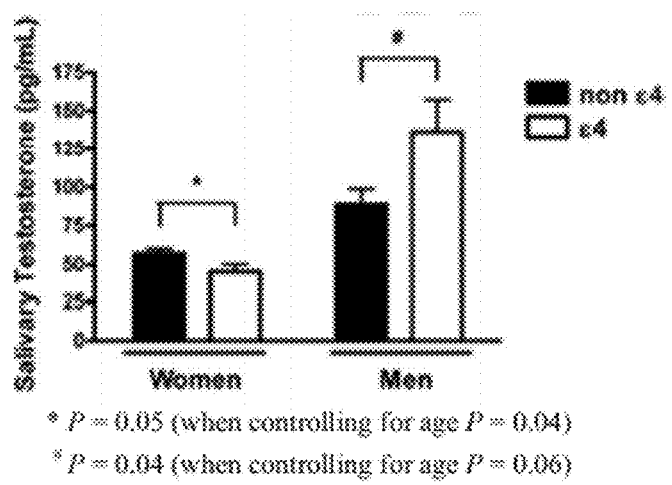
FIG. 14 is a chart showing, for elderly women and men, effect of ε4 on salivary testosterone levels.

6. Salivary Cortisol and Testosterone Levels and Correlations with Cognitive Performance FIG. 14 is a chart showing, for elderly women and men, effect of ε4 on salivary testosterone levels. Effects were identified for sex (F=3.944, p=0.05 and F=4.245, p=0.04 after controlling for age, FIG. 14) and ε4 (F=4.520, p=0.04 and F=4.036, p=0.06 after controlling for age, FIG. 14) on salivary testosterone levels. Women carrying ε4 had lower testosterone levels compared with non-carriers while men carrying ε4 had higher testosterone levels compared with non-carriers. Age was included as a covariate in the analysis.

Based on this result and to avoid spurious conclusions, potential correlations of salivary testosterone levels with cognitive measures in the complete sample were not considered. Only in men, salivary cortisol levels correlated with some cognitive measures. (See Table 4.)

TABLE 4

Correlations of salivary cortisol levels with cognitive measures.

| | | Cortisol Level | | | |
|---|---|---|---|---|---|
| Measure | | Women | Men | Non ε4 | ε4 |
| MMSE[a] | | −0.05 | −0.32 | −0.05 | −0.22 |
| BAI | | 0.05 | 0.12 | 0.03 | 0.39 |
| WRAT-R | | −0.08 | 0.03 | −0.03 | −0.14 |
| Reaction times[b] | | 0.16 | −0.33 | 0.05 | −0.10 |
| Spatial span[c] | SSF | 0.00 | 0.27 | 0.03 | 0.03 |
| | SSB | −0.03 | −0.11 | −0.11 | 0.05 |
| Faces[d] | Faces immediate | 0.04 | −0.22 | 0.03 | −0.17 |
| | Faces delayed | −0.11 | −0.23 | −0.04 | −0.49$ |
| Family Pictures | Family Pictures immediate | −0.08 | −0.07 | 0.05 | −0.23 |
| | Family Pictures delayed | −0.03 | −0.15 | 0.04 | −0.15 |
| NINL[a] | No change immediate | −0.08 | −0.06 | −0.09 | 0.02 |
| | No change delayed | −0.09 | −0.02 | −0.08 | −0.07 |
| | Novel image immediate | −0.05 | −0.45* | −0.12 | −0.14 |
| | Novel image delayed | −0.01 | −0.37+ | −0.07 | −0.05 |
| | Novel Location immediate | −0.02 | −0.28 | 0.06 | −0.38 |
| | Novel Location delayed | 0.02 | −0.12 | 0.08 | −0.14 |
| | Total NINL I | −0.07 | −0.004* | −0.08 | −0.31 |
| | Total NINL II | −0.03 | −0.33 | −0.04 | −0.14 |
| Memory Island visible target session[e] | Average velocity | −0.05 | 0.10 | −0.03 | −0.16 |
| | Total distance | −0.21 | 0.36 | −0.03 | −0.30 |
| | % Successful trials | 0.11 | 0.05 | 0.07 | 0.20 |
| | % In target quadrant | 0.20 | −0.09 | 0.14 | 0.04 |
| | Cumulative distance | −0.08 | 0.01 | −0.06 | 0.03 |
| Memory Island hidden target session[f] | Average velocity | −0.09 | 0.05 | −0.13 | 0.00 |
| | Total distance | 0.09 | 0.21 | 0.09 | 0.22 |
| | % Successful trials | −0.18 | −0.24 | −0.19 | −0.41 |
| | % In target quadrant | −0.21 | −0.11 | −0.19 | −0.30 |
| | Cumulative distance | 0.13 | 0.32 | 0.17 | 0.43 |

[a]N = 109; missing four cortisol samples, two outliers removed.
[b]N = 107; two outliers removed.
[c]N = 104; five participants dropped out of the study between the two testing times, one missing score.
[d]N = 108; missing one score.
[e]N = 103; six participants did not complete the visible target session.
[f]N = 80; 29 did not complete the hidden target session.
*Correlation is significant at the 0.05 level (two-tailed).
$While p < 0.05, closer examination showed it was driven by a single datapoint (P = 0.187 without).
+p = 0.051.

Figure 15:
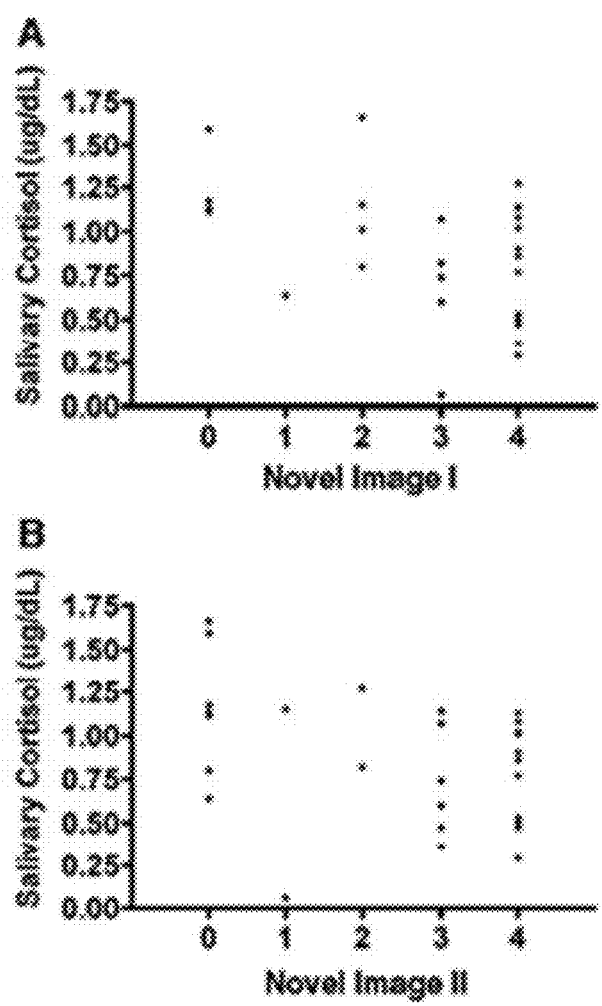
FIGS. 15A and 15B are charts showing, for elderly men, correlation of salivary cortisol levels with NINL I novel image recognition, and correlation of salivary cortisol levels with NINL II novel image recognition, respectively, according to one or more described embodiments.

FIGS. 15A and 15B are charts showing, for elderly men, correlation of salivary cortisol levels with NINL I novel image recognition, and correlation of salivary cortisol levels with NINL II novel image recognition, respectively. In the object recognition tests, Novel Image sub-scores correlated with salivary cortisol levels; immediate scores (r=−0.45, p=0.05, FIG. 12A), and delayed scores (r=−0.37, p=0.05, FIG. 15B). Total NINL scores correlated also with salivary cortisol levels (r=−0.44, p=0.05). No such correlations were found in women.

TABLE 5

Effects of ε4 and sex on cognitive measures (repeated-measures analyses)[a]

| | | ε4 | | Sex | | Within subject[b] | | Interaction | | | |
|---|---|---|---|---|---|---|---|---|---|---|---|
| | | | | | | | | ε4 × Seq | | Sex × Seq | |
| Measure | N | F | P | F | P | F | P | F | P | F | P |
| Faces[c] | 114 | 0.01 | 0.943 | 1.00 | 0.320 | 6.91 | 0.010 | 0.15 | 0.696 | 0.90 | 0.344 |
| Family Pictures | 115 | 2.50 | 0.117 | 22.57 | <.0001 | 0.12 | 0.733 | 1.73 | 0.191 | 3.64 | 0.059 |
| Visible Velocity | 109 | 0.31 | 0.861 | 8.15 | 0.005 | 3.58 | 0.036 | 1.82 | 0.170 | 2.11 | 0.131 |
| Visible Total Distance | 109 | 0.77 | 0.781 | 3.24 | 0.075 | 0.50 | 0.535 | 0.11 | 0.818 | 0.61 | 0.486 |
| Visible Latency | 109 | 3.26 | 0.074 | 0.65 | 0.421 | 0.33 | 0.639 | 2.14 | 0.138 | 0.50 | 0.537 |
| Visible % Time spent in Target | 109 | 1.07 | 0.303 | 3.73 | 0.056 | 2.18 | 0.117 | 0.93 | 0.392 | 0.69 | 0.496 |
| Visible % Successful trials | 109 | 2.06 | 0.154 | 0.05 | 0.821 | 1.03 | 0.353 | 1.14 | 0.317 | 0.01 | 0.987 |

TABLE 5-continued

Effects of ∈4 and sex on cognitive measures (repeated-measures analyses)[a]

| | | ∈4 | | Sex | | Within subject[b] | | Interaction ∈4 × Seq | | Sex × Seq | |
|---|---|---|---|---|---|---|---|---|---|---|---|
| Measure | N | F | P | F | P | F | P | F | P | F | P |
| Visible Cumulative Distance | 109 | 0.18 | 0.670 | 0.55 | 0.462 | 0.34 | 0.695 | 2.00 | 0.142 | 0.69 | 0.493 |
| Hidden Velocity | 84 | 2.37 | 0.128 | 3.40 | 0.069 | 2.89 | 0.059 | 0.10 | 0.905 | 1.91 | 0.151 |
| Hidden Total Distance | 84 | 1.10 | 0.297 | 1.00 | 0.321 | 0.02 | 0.983 | 0.84 | 0.433 | 1.12 | 0.331 |
| Hidden Latency | 84 | 6.17 | 0.015 | 0.69 | 0.410 | 1.01 | 0.366 | 0.83 | 0.438 | 2.40 | 0.094 |
| Hidden % Time spent in Target | 84 | 3.48 | 0.066 | 0.76 | 0.385 | 1.33 | 0.268 | 1.25 | 0.288 | 1.18 | 0.311 |
| Hidden % Successful trials | 84 | 2.06 | 0.154 | 0.05 | 0.821 | 1.03 | 0.353 | 1.14 | 0.317 | 0.01 | 0.987 |
| Hidden Cumulative Distance | 84 | 5.14 | 0.026 | 0.62 | 0.433 | 0.73 | 0.482 | 0.21 | 0.809 | 2.60 | 0.078 |

[a]There were 19 models in Table 5. Since there were 19 separate models for different outcomes (response variables), a multiple test procedure for controlling the family-wise error rate was not applied when testing general hypotheses defined in terms of sub-models. Age was used as a covariate in all analyses.
[b]Repeated measures analyses were used to assess potential within-subjects effects.
[c]Faces represented a combined measure of "Faces I and Faces II."

TABLE 6

Effects of ∈4 and sex on cognitive measures (GEE regression analysis)[a]

| | | ∈4 | | Sex | | Within subject[b] | | Interaction ∈4 × Seq[c] | | Sex × Seq | |
|---|---|---|---|---|---|---|---|---|---|---|---|
| Measure | N | $\chi^2$ | P | $\chi^2$ | P | $\chi^2$ | P | $\chi^2$ | P | $\chi^2$ | P |
| NINL total | 115 | 4.23 | 0.040 | 2.51 | 0.113 | 3.48 | 0.062 | 4.93 | 0.026 | 0.09 | 0.767 |
| Novel location | 115 | 4.01 | 0.045 | 4.82 | 0.028 | 0.09 | 0.763 | 1.82 | 0.178 | 0.52 | 0.472 |
| Novel image | 115 | 1.66 | 0.198 | 0.25 | 0.615 | 5.30 | 0.021 | 0.65 | 0.419 | 0.70 | 0.403 |
| No change | 115 | 0.00 | 0.968 | 0.13 | 0.723 | 0.00 | 0.980 | 7.64 | 0.006 | 1.44 | 0.230 |

[a]Adjustment for multiple testing was handled using repeated-measures analyses. Age was used as a covariate in all analyses.
[b]Repeated-measures analyses were used to assess potential within-subject effects.
[c]Sequential, used for the assessments of potential interactions of ∈4 or sex with the repeated measure of performance.

C. Discussion

The established cognitive tests Faces, Family Pictures, SSF and SSB were administered along with the object recognition and spatial navigation tests to non-demented elderly. Women performed better than men in the family pictures test (FIG. 10A). This sex difference in performance is consistent with the better performance of women than men in recognizing pictures containing natural categories. Of the cognitive tests used, only the object recognition and spatial navigation tests were sensitive to effects of ∈4 on cognitive performance. The lack of ∈4 effects in the established cognitive tests is consistent with other studies showing no effects of ∈4 on cognitive performance in the non-demented elderly. Deficits in episodic memory, memory for specific experiences that can be defined in terms of time and space, are often the first symptoms experienced by patients with AD. Therefore, poor performance on episodic memory tests such as the object recognition and spatial navigation tests can indicate pre-clinical phases of cognitive impairment.

In the object recognition test, an effect was identified for ∈4 (FIG. 10C) on the novel location score (combined immediate and delayed score) with ∈4 carriers performing worse on novel location, but not on novel object, scores than non-∈4 carriers. These data indicate that it is more difficult for ∈4 carriers to accurately recall location. Together with the poorer performance of ∈4 than non-∈4 carriers on the spatial navigation test, these data support the proposition that ∈4 carriers are particularly susceptible to spatial memory impairments.

In the object recognition test, there was also an effect of sex (FIG. 10D) on the novel location score (combined immediate and delayed score) with women performing better than men, and there were no effects of sex on spatial navigation in the Memory Island test. Using the same object recognition test, for cognitive testing of healthy adult humans, no sex differences in performance were seen. In the first series of trials, using the same spatial navigation test used in the current study, adult men performed better than adult women.

In the probe trial, elderly women and men did not spend most of their time in the target quadrant. (See FIG. 13A.) In contrast, younger adult women and men (20-44 years of age) did spend most of their time in the target quadrant in the probe trial. (Section VI.) These data are consistent with the effect of age on spatial memory retention in young (25-45 years of age), middle-aged (45-65 years of age), and old (65-93 years of age) humans shown in other studies, with the older study participants showing lower measures of spatial memory retention in the probe trial than the younger study participants. In the probe trial, ϵ4 carriers spent more time in the right quadrant than the target quadrant (FIG. 13B). This was not seen in non-ϵ4 carriers. This is an important finding in that, based on the starting orientation in the probe trial, entering the right quadrant indicates that the study participants navigated straight rather than effectively searching for the target location.

For salivary testosterone levels, there was a sex×ϵ4 interaction, with higher salivary testosterone levels in ϵ4-carrying than non-ϵ4-carrying men and lower salivary testosterone levels in ϵ4-carrying than non-ϵ4-carrying women. (See FIG. 14.) In men, the difference between immediate and delayed novel image recognition scores correlated with salivary testosterone levels ($r=0.473$, $p=0.015$) and at each performance level difference between immediate and delayed recognition performance, ϵ4-carrying men had the highest salivary testosterone levels. Similarly, during the hidden target session of Memory Island, salivary testosterone levels in male ϵ4 carriers correlated with latency ($r=-0.92$, $p=0.03$), cumulative distance to the target location ($r=0.87$, $p=0.06$), percentage of successful trials ($r=0.85$, $p=0.07$), and percentage of time spent in the target quadrant ($r=0.89$, $p=0.04$).

The correlations of salivary cortisol levels with cognitive measures were sensitive to sex. Only in men, salivary cortisol levels correlated with immediate total NINL scores, and immediate Novel Image sub-scores. (See Table 6.) The association of higher cortisol levels with poorer cognitive performance in the elderly is consistent with other studies. However, the second series of trials underlines the importance of considering ϵ4 and sex in assessing potential correlations of cortisol with cognitive measures.

There was no significant sex difference in the proportion of ϵ4 carriers. The lack of such a difference might have been due to the sex difference in sample size with more women than men participating in the study, which in turn might relate to sex differences in longevity.

D. Conclusion

The object recognition and spatial navigation tests were sensitive to effects of ϵ4 in the elderly. Differences in neuroanatomy, brain glucose metabolism during mental activity, and brain activation in memory tasks between non-demented non-ϵ4 and ϵ4 carriers might contribute to these effects. As the mean age of the participants of this study was 82, these data indicate that while the ϵ4-associated risk to develop AD is age-dependent and maximal before this age, effects of ϵ4 on cognitive performance can be revealed in the old-old using episodic memory tests.

VIII. APOE ϵ4 EFFECTS ON SPATIAL LEARNING AND MEMORY IN CHILDREN

This section describes example implementations as well as discussion of specific problems addressed and advantages for those implementations in some contexts. Alternatively, implementations of the preceding techniques and tools vary in terms of technical details, specific advantages and/or problems solved.

Compared to APOE ϵ3, APOE ϵ4 is a risk factor for age-related cognitive decline and cognitive impairments following environmental challenges. To assess whether APOE ϵ4 has effects on cognitive performance in children, they were given standardized cognitive tests as well as an object recognition test and a spatial navigation test sensitive to effects of APOE ϵ4 in the elderly. Children with APOE ϵ4 showed reduced novel location recognition, reduced ability to navigate to a visible target, and reduced spatial memory retention. The early effect of APOE ϵ4 on cognition indicates predisposition to cognitive impairments later in life.

Of the three major human APOE isoforms, which play roles in cholesterol metabolism and are encoded by distinct alleles (ϵ2, ϵ3, and ϵ4), ϵ4 increases the risk of age-related cognitive decline and cognitive injury following environmental insults. To assess potential effects of ϵ4 on cognition in children, 55 healthy 7-10 year-olds (girls: 17 non-ϵ4 and eight -ϵ4; boys: 24 non-ϵ4 and six -ϵ4) were given established cognitive tests, as well as an object recognition test and a spatial navigation test requiring navigation sensitive to effects of ϵ4 in non-demented elderly, and provided saliva samples for APOE genotyping and cortisol levels.

The inclusion criteria were healthy boys and girls 7-10 years of age. The exclusion criteria were children whose birth mother or legal guardian could not be interviewed, children with severe visual impairments, children born more than 35 weeks premature, children with epilepsy, head injury, Tourette's syndrome, cerebral palsy, congenital abnormalities, severe brain trauma, diagnosed with leukemia or any other medical condition that could interfere with cognitive ability, or children exposed to elicit drugs during pregnancy. Children were from middle/upper class families and 84% Caucasian, 7% Hispanic, 3.5% African American, and 3.5% Pacific Islander. During pregnancy the average age of the mother's was 29 years old with 12.0% reporting smoking and 17.2% reporting at least some alcohol consumption during pregnancy.

Average cortisol levels did not correlate with any cognitive measure, but did correlate with anxiety scores (Pearson Correlation $r=0.293$, $p<0.05$). (See Table 7, below.) Thus, self-reported anxiety levels were likely not a confounding factor for assessing cognitive measures. Each child was given cognitive tests during a 1.5 hr session. (See Table 7, below.)

TABLE 7

Cognitive measures in non-ϵ4 and ϵ4 carrying 7-10 year-old boys and girls.

| Task | Immediate | | Delay | | ANCOVA or REM (Geno)[1] | |
|---|---|---|---|---|---|---|
| | Non-ϵ4 | ϵ4 carrier | Non-ϵ4 | ϵ4 carrier | F | p |
| Dot Location[a]— Learning | 10.4 + 0.5 | 11.6 + 0.9 | | | 1.37 | 0.25 |

TABLE 7-continued

Cognitive measures in non-ε4 and ε4 carrying 7-10 year-old boys and girls.

| | Immediate | | Delay | | ANCOVA or REM (Geno)[1] | |
|---|---|---|---|---|---|---|
| Task | Non-ε4 | ε4 carrier | Non-ε4 | ε4 carrier | F | p |
| Dot Location—Total Score | 11.01 + 0.5 | 12.4 + 0.9 | | | 1.95 | 0.17 |
| Dot Location—Long Delay | 11.6 + 0.3 | 11.8 + 0.6 | | | 0.05 | 0.81 |
| Dot Location—Short Delay | 11.3 + 0.4 | 12.0 + 0.7 | | | 0.67 | 0.41 |
| CPT[b] Non-clinical score | 56.6 + 3.1 | 55.1 + 5.4 | | | 0.05 | 0.81 |
| CPT % Omissions | 49.6 + 2.2 | 51.8 + 3.8 | | | 0.24 | 0.62 |
| CPT % Commissions | 49.6 + 1.9 | 45.9 + 3.3 | | | 0.98 | 0.32 |
| CPT Hit Rate | 47.6 + 1.8 | 52.0 + 3.1 | | | 1.47 | 0.23 |
| MASC[c]—Total Score | 45.5 + 2.3 | 47.4 + 3.9 | | | 0.17 | 0.67 |
| WASI[d] Vocabulary | 56.9 + 1.8 | 57.3 + 3.1 | | | 0.01 | 0.91 |
| WASI Block Design | 56.2 + 1.6 | 60.5 + 2.8 | | | 1.64 | 0.20 |
| Family Pictures | 11.8 + 0.4 | 11.9 + 0.5 | 10.0 + 0.8 | 10.2 + 0.9 | 3.39 | 0.07 |
| NINL—Total Score | 27.4 + 1.0 | 26.0 + 1.0 | 25.5 + 1.8 | 23.7 + 1.8 | 1.19 | 0.28 |
| NINL—Novel Image | 5.1 + 0.4 | 4.2 + 0.5 | 5.2 + 0.7 | 4.8 + 0.8 | 0.10 | 0.74 |
| NINL—Novel Location | 6.5 + 0.4 | 6.1 + 0.4 | 5.3 + 0.6 | 4.3 + 0.7 | 4.77[e] | 0.03[e] |
| Average Cortisol levels (ug/dL) | 0.07 + 0.01 | 0.08 + 0.02 | | | 0.80 | 0.38 |

[a]Childrens' Memory Scale, Dot Location test.
[b]Conners' Continuous Performance Test ("CPT") is an attention test used in ADHD research and clinical assessments.
[c]Multi-dimensional Anxiety Scale for Children.
[d]Wechsler Abbreviated Scale of Intelligence.
[e]Particularly significant effects As attention (CPT, overall non-clinical score) correlated with performance in most cognitive tests (p<0.05), it was included as a covariate in all analyses. Age was used as a covariate if age correction tables were not available. The data were analyzed using ANCOVAs or repeated measures (REM) with trial as the with-in subject variable and genotype as the fixed factor. As no statistically significant effects were identified for sex on any cognitive measure, boys and girls were combined for the analysis. ε4 did not affect general cognitive ability in children (Table 7), consistent with earlier reports. However, an effect was identified for ε4 on novel location recognition (p<0.04) with lower delayed novel location recognition scores in ε4 carriers (p<0.03). As such an effect of ε4 was also seen in non-demented healthy elderly, novel location recognition can be used to detect effects of ε4 throughout life.

Figure 16:
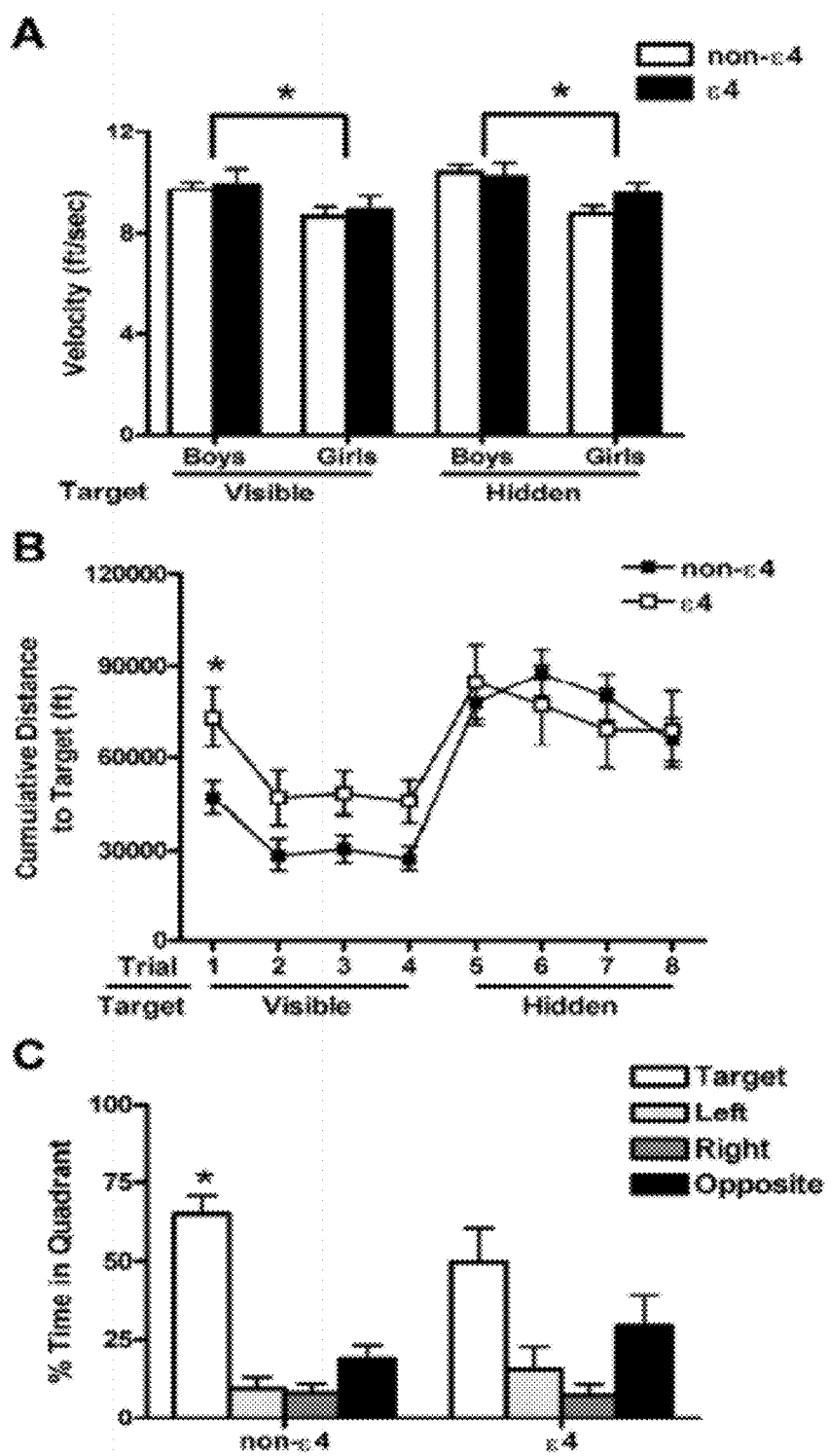
FIGS. 16A, 16B and 16C are charts showing effects of APOE ε4 on performance in 7-10 year-old boys and girls tested with a virtual reality, spatial navigation software tool, according to one or more described embodiments.

Spatial learning and memory requiring navigation were assessed using the virtual reality Memory Island test. FIGS. 16A, 16B and 16C show effects of ε4 on Memory Island performance in 7-10 year-old boys and girls. FIG. 16A shows effects of sex on velocity during the visible and hidden target trials (*p<0.04). FIG. 16B shows effects of ε4 on cumulative distance to the target in the visible (*p<0.005), but not hidden, target trials. FIG. 16C shows percentage of time spend in quadrants for ε4 and non-ε4 children (*p<0.04 for the target quadrant versus all other quadrants). Compared to the left and right quadrants, the children tended to spend more time in the opposite quadrant. This might be due to the fact that the start orientation in the probe trial faces the opposite quadrant.

The velocity of boys was higher than girls during the trials with the visible (F=4.75; p<0.04) and hidden (REM ANCOVAs F=7.90; p<0.007) target. (See FIG. 16A.) Therefore, velocity was used as covariate for the analyses of performance on Memory Island. Non-ε4 carriers outperformed ε4 carriers during the trials with the visible (F=4.53; p<0.04), but not hidden (F=0.11; p=0.74), target by navigating closer to the visible target location. (See FIG. 16B.)

Fifteen minutes following the last hidden trial, non-ε4 carriers showed spatial memory retention in the probe trial (no target present) and searched most of the time in the quadrant previously containing the target (p<0.04) but ε4 carriers did not. (See FIG. 16C.) Similarly, while 75.6% of non-ε4 carriers showed target preference, only 43% of ε4 carriers did (p<0.04, Fisher's exact test).

Thus, effects of ε4 on spatial learning and memory are already detected in 7-10 year-old children and indicate predisposition to cognitive injury following environmental challenges and/or age-related cognitive decline.

IX. COGNITIVE STATUS ASSESSMENT AND THERAPEUTIC INTERVENTION EXAMPLES

Example 1

In this example, the cognitive status of an elderly subject suspected to have dementia (e.g., an age-associated dementia, such as Alzheimer's disease) is assessed. The subject is given the Memory Island and NINL tests described herein. The subject's performance on the Memory Island test (e.g., distance traversed, time elapsed before reaching target, percentage of successful trials, time spent in target area, velocity of movement) and NINL tests (e.g., Novel Location score, Novel Image score, No Change score, total NINL score) is compared with previously measured performance benchmarks for non-demented individuals of the same sex and similar age.

Example 2

In this example, the cognitive status of an elderly subject suspected to have age-associated dementia is assessed over time. The subject is initially given Memory Island and NINL tests described herein. The subject's performance on the Memory Island and NINL tests is compared with previously measured performance benchmarks for non-demented individuals of the same sex and similar age. One year later, the subject is given a second round of Memory Island and NINL tests. The subject's performance on the Memory Island and NINL tests is compared with the subject's own performance the previous year.

Example 3

In this example, the cognitive status of a child subject suspected to have a genetic predisposition toward dementia later in life (for example an age-associated dementia, such as Alzheimer's disease) is assessed. The child subject is given the Memory Island and NINL tests described herein. The child subject's performance on the Memory Island and NINL tests is compared with previously measured performance benchmarks for non-demented individuals of the same sex and similar age.

Example 4

In this example, a subject who has been diagnosed with dementia (for example an age-associated dementia, such as Alzheimer's disease) is given the Memory Island and NINL tests described herein. Baseline measures are determined (for Memory Island: distance traversed, time elapsed before reaching target, percentage of successful trials, time spent in target area, velocity of movement; for NINL: Novel Location score, Novel Image score, No Change score, total NINL score), and the subject is given an anti-Alzheimer's drug (such as Donepezil (ARICEPT) or anti-APOE ε4 drug) as a therapeutic intervention.

For a subject given Donepezil, the subject is treated with 5 mg per day of the drug for a period of at least four to six weeks, and then the subject is once again given the Memory Island and NINL tests. If a desired improvement in scores is not obtained, then the dose of the drug is increased to 10 mg per day. Testing with the Memory Island and NINL tests is then repeated to assess the response to the drug, where a change in test scores indicates a response to the drug.

Example 5

In this example, a subject who has been diagnosed with dementia (for example an age-associated dementia, such as Alzheimer's disease) is given the Memory Island and NINL tests described herein. Baseline measures are determined as described in Example 4, and the subject is given an anti-Alzheimer's drug (such as Donepezil (ARICEPT) or anti-APOE ε4 drug) as a therapeutic intervention.

For a subject given Donepezil, the subject is treated with 5 mg per day of the drug for a period of at least four to six weeks, and then the subject is once again given the Memory Island and NINL tests. If a desired improvement in scores is not obtained, the subject is given a different drug. Testing with the Memory Island and NINL tests is then repeated to assess the response to the different drug, where a change in test scores indicates a response to the different drug.

Having described and illustrated the principles of my invention with reference to various described embodiments, it will be recognized that the described embodiments can be modified in arrangement and detail without departing from such principles. It should be understood that the programs, processes, or methods described herein are not related or limited to any particular type of computing or clinical environment, unless indicated otherwise. Various types of general purpose or specialized computing environments may be used with or perform operations in accordance with the teachings described herein. Elements of the described embodiments shown in software may be implemented in hardware and vice versa.

In view of the many possible embodiments to which the principles of my invention may be applied, I claim as my invention all such embodiments as may come within the scope and spirit of the following claims and equivalents thereto.

I claim:

1. A method comprising:
   receiving input from a user as the user takes a test in which the user identifies novel images in a virtual reality environment executing on a computer, if any, and novel quadrant locations of images, if any, among a first ordered set of two or more image panels presented to the user in series relative to a second ordered set of image panels presented to the user in series, wherein an image panel comprises at least three different images, and wherein the input comprises an indication of no change or change between an image panel in the first ordered set and an image panel from a same order position in the second ordered set as an order position of the image panel in the first ordered set;
   measuring performance of the user in the test based at least in part upon the received input; and
   using the measured performance of the user on the test in analysis of cognitive status.

2. The method of claim 1, wherein at least one image panel of the first ordered set is displayed between image panels being compared from the first ordered set and the second ordered set.

3. The method of claim 1, wherein the change between an image panel in the second ordered set is a novel quadrant location.

4. The method of claim 1, wherein the change between an image panel in the second ordered set is a change in image content for one of the three images in an image panel.

5. The method of claim 1, wherein the measured performance includes a novel location score indicating performance of the user in identifying changes in locations of images.

6. The method of claim 1, wherein the measured performance includes a novel image score indicating performance of the user in identifying new images in the second ordered set relative to the first ordered set.

7. The method of claim 1, wherein the measured performance includes a no change score indicating performance of the user in identifying situations with no change in image content or image location for the second ordered set relative to the first ordered set.

8. The method of claim 1, wherein the analysis of cognitive status further comprises measuring neural activity of the user with a magnetic resonance imaging tool as the user takes the test.

9. A method comprising:
displaying to a user, in a virtual reality environment executing on a computer, a first ordered set of two or more image panels in series, wherein each image panel includes a plurality of images;
after the series of the first ordered set of images is displayed, displaying a second ordered set of two or more image panels that correspond to the first set of image panels, wherein at least one of the second ordered set of image panels has one of the images associated therewith in a novel location on the image panel when compared to the first ordered set of images;
receiving input from the user indicating the novel location; and
measuring performance of the user based at least in part upon the received input to analyze cognitive status.

10. The method of claim 9, wherein a first image panel from the first ordered set is compared to a first image panel from the second ordered set, and wherein at least a second image panel from the first ordered set is displayed in between the first image panel from the first ordered set and the first image panel from the second ordered set.

11. The method of claim 9, wherein each image panel has four quadrants and wherein the novel location includes displaying an image in a different quadrant in the second ordered set of images than was displayed in the first ordered set.

12. The method of claim 9, wherein the measured performance includes a novel location score indicating performance of the user in identifying a change in location of an image.

13. The method of claim 9, wherein the measured performance includes a novel image score indicating performance of the user in identifying at least one new image in the second ordered set relative to the first ordered set.

14. The method of claim 9, wherein the measured performance includes a no change score indicating performance of the user in identifying situations with no change in image content or image location for the second ordered set relative to the first ordered set.

15. The method of claim 9, wherein the analysis of cognitive status further comprises measuring neural activity of the user with a magnetic resonance imaging tool as the user takes the test.

16. A system comprising:
a virtual reality environment executing on a computer including a processor for displaying a first ordered set of two or more image panels in series, wherein each image panel includes a plurality of images and, after the series of the first ordered set of images is displayed, for displaying a second ordered set of two or more image panels that correspond to the first set of image panels, wherein at least one of the second ordered set of image panels has one of the images associated therewith in a novel location on the image panel when compared to the first ordered set of images;
a user input device for receiving input from the user indicating the novel location; and
the processor for measuring performance of the user based at least in part upon the received input to analyze cognitive status.

* * * * *